(12) United States Patent
Goldberg et al.

(10) Patent No.: US 9,260,367 B2
(45) Date of Patent: Feb. 16, 2016

(54) METHODS OF CONVERTING POLYOLS

(71) Applicant: University of Washington through its Center for Commercialization, Seattle, WA (US)

(72) Inventors: Karen I. Goldberg, Seattle, WA (US); D. Michael Heinekey, Seattle, WA (US); Nandita Malathi Weliange, RoseBay (AU); Takiya J. Ahmed Foskey, Midland, MI (US); Eric R. Camp, Mountlake Terrace, WA (US); Gene Wong, Seattle, WA (US); David Lao, Seattle, WA (US)

(73) Assignee: Univesity of Washington Through Its Center For Communication, Seattle, WA (US)

( * ) Notice: Subject to any disclaimer, the term of this patent is extended or adjusted under 35 U.S.C. 154(b) by 0 days.

(21) Appl. No.: 14/475,300

(22) Filed: Sep. 2, 2014

(65) Prior Publication Data
US 2014/0371493 A1    Dec. 18, 2014

Related U.S. Application Data

(63) Continuation of application No. PCT/US2013/028618, filed on Mar. 1, 2013.

(60) Provisional application No. 61/606,103, filed on Mar. 2, 2012.

(51) Int. Cl.
*C07C 29/60*     (2006.01)
*B01J 31/18*     (2006.01)

(52) U.S. Cl.
CPC . *C07C 29/60* (2013.01); *B01J 31/18* (2013.01)

(58) Field of Classification Search
CPC ....................................................... C07C 29/60
See application file for complete search history.

(56) References Cited

U.S. PATENT DOCUMENTS

| | | | |
|---|---|---|---|
| 4,642,394 | A | 2/1987 | Che |
| 6,080,898 | A | 6/2000 | Drent et al. |
| 6,841,085 | B2 | 1/2005 | Werpy et al. |
| 7,126,032 | B1 | 10/2006 | Aiken |
| 2002/0077511 | A1 | 6/2002 | Bullock et al. |
| 2004/0181104 | A1 | 9/2004 | Yeh et al. |
| 2010/0236984 | A1 | 9/2010 | Brookhart et al. |

OTHER PUBLICATIONS

International search report and written opinion dated May 13, 2013 for PCT/US2013/028681.
Nanda, et al. Purification of crude glyceroal using acidification: effects of acid types and product characterization. Austin J Chem Eng. 2014; 1:1-7.
Chaminand, J. et al. (2004) "Glycerol hydrogenolysis on heterogeneous catalysts," Green Chemistry, 6(8):359-361.
Chheda, J.N. et al. (2007) "Liquid-Phase Catalytic Processing of Biomass-Derived Oxygenated Hydrocarbons to Fuels and Chemicals," Angewandte Chemie International Edition, 46:7164-7183.
Corma, A. et al. (2007) "Chemical Routes for the Transformation of Biomass into Chemicals," Chemical Reviews, 107(6):2411-2502.
Daniel, O.M. et al. (2010) "X-ray Absorption Spectroscopy of Bimetallic Pt—Re Catalysts for Hydrogenolysis of Glycerol to Propanediols," ChemCatChem, 2(9):1107-1114.
Dasari, M.A. et al. (2005) "Low-pressure hydrogenolysis of glycerol to propylene glycol," Applied Catalysis A: General, 281(1-2):225-231.
Dykeman, R.R. et al. (2007) "Catalytic deoxygenation of terminal-diols under acidic aqueous conditions by the ruthenium complexes [(η6-arene)Ru(X)(N ∩ N)](OTf)n, X=H2O, H, η6-arene=p-Me-iPr-C6H4, C6Me6, N ∩ N=bipy, phen, 6,6'-diamino-bipy, 2,9-diamino-phen, n=1, 2): Influence of the ortho-amine substituents on catalytic activity," Journal of Molecular Catalysis A: Chemical, 277(1-2):233-251.
Ghosh, P. et al. (2009) "Synthesis of Ruthenium Carbonyl Complexes with Phosphine or Substituted Cp Ligands, and Their Activity in the Catalytic Deoxygenation of 1,2-Propanediol," Inorganic Chemistry, 48(14):6490-6500.
Gong, L. et al. (2010) "Selective hydrogenolysis of glycerol to 1,3-propanediol over a Pt/WO$_3$/TiO$_2$/SiO$_2$ catalyst in aqueous media," Applied Catalysis A: General, 390(1-2):119-126.
Göttker-Schnetmann, I. et al. (2004) "Synthesis and Properties of Iridium Bis(phosphinite) Pincer Complexes (p-XPCP)IrH$_2$, (p-XPCP)Ir(CO), (p-XPCP)Ir(H)(aryl), and {(p-XPCP)Ir}$_2${μ-N$_2$} and Their Relevance in Alkane Transfer Dehydrogenation," Organometallics, 23(8):1766-1776.
Gupta, M. et al. (1997) "Catalytic Dehydrogenation of Cycloalkanes to Arenes by a Dihydrido Iridium P—C—P Pincer Complex," Journal of the American Chemical Society, 119(4):840-841.
Harmer, M.A. et al. (2010) "Renewably sourced polytrimethylene ether glycol by superacid catalyzed condensation of 1,3-propanediol," Green Chemistry, 12(8):1410-1416.
Kusunoki, Y. et al. (2005) "Highly active metal—acid bifunctional catalyst system for hydrogenolysis of glycerol under mild reaction conditions," Catalysis Communications, 6(10):645-649.
Miyazawa, T. et al. (2006) "Glycerol conversion in the aqueous solution under hydrogen over Ru/C + an ion-exchange resin and its reaction mechanism," Journal of Catalysis, 240(2):213-221.
Miyazawa, T. et al. (2007) "Development of a Ru/C catalyst for glycerol hydrogenolysis in combination with an ion-exchange resin," Applied Catalysis A: General, 318:244-251.
Montassier, C. et al. (1995) "Deactivation of supported copper based catalysts during polyol conversion in aqueous phase," Applied Catalysis A: General, 121(2):231-244.
Nakagawa, Y. et al. (2010) "Direct hydrogenolysis of glycerol into 1,3-propanediol over rhenium-modified iridium catalyst," Journal of Catalysis, 272(2):191-194.
Nakagawa, Y. et al. (2011) "Heterogeneous catalysis of the glycerol hydrogenolysis," Catalysis Science & Technology, 1:179-190.

(Continued)

*Primary Examiner* — Brian J Davis
(74) *Attorney, Agent, or Firm* — Wilson Sonsini Goodrich & Rosati

(57) ABSTRACT

Methods for converting polyols are provided. The methods provided can include using a metal pincer catalyst (e.g., an iridium pincer catalyst) to remove at least one alcohol group from a polyol. The methods provided can include converting glycerol to 1,3-propanediol.

21 Claims, 4 Drawing Sheets

(56) References Cited

OTHER PUBLICATIONS

Oh, J. et al. (2011) "Selective conversion of glycerol to 1,3-propanediol using Pt-sulfated zirconia," Green Chemistry, 13(8):2004-2007.

Pagliaro, M. et al. (2007) "From Glycerol to Value-Added Products," Angewandte Chemie International Edition, 46(24):4434-4440.

Perosa, A. and P. Tundo (2005) "Selective Hydrogenolysis of Glycerol with Raney Nickel," Industrial & Engineering Chemistry Research, 44(23):8535-8537.

Qin, L-Z. et al. (2010) "Aqueous-phase deoxygenation of glycerol to 1,3-propanediol over Pt/$WO_3$/$ZrO_2$ catalysts in a fixed-bed reactor," Green Chemistry, 12(8):1466-1472.

Schlaf, M. (2006) "Selective deoxygenation of sugar polyols to α,ω-diols and other oxygen content reduced materials a new challenge to homogeneous ionic hydrogenation and hydrogenolysis catalysis," Dalton Transactions, 39:4645-4653.

Schlaf, M. et al. (2001) "Metal-Catalyzed Selective Deoxygenation of Diols to Alcohols," Angewandte Chemie International Edition, 40(20):3887-3890.

Schlaf, M. et al. (2009) "Bioenergy II: Group 8 Metal Complexes as Homogeneous Ionic Hydrogenation and Hydrogenolysis Catalysts for the Deoxygenation of Biomass to Petrochemicals—Opportunities, Challenges, Strategies and the Story so Far," International Journal of Chemical Reactor Engineering, 7(1):A34, 13 pages.

Schlaf, M. et al. (2009) "Catalytic Deoxygenation of 1,2-Propanediol to Give $n$-Propanol," Advanced Synthesis & Catalysis, 351(5):789-800.

Tanaka, R. et al. (2009) "Catalytic Hydrogenation of Carbon Dioxide Using Ir(III)—Pincer Complexes," Journal of the American Chemical Society, 131(40):14168-14169.

Xie, Z. And M. Schlaf (2005) "Direct transformation of terminal vic-diols to primary alcohols and alkanes through hydrogenation catalyzed by [cis-Ru(6,6'-C12-bipy)2(OH2)2](CF3SO3)2 in acidic medium," Journal of Molecular Catalysis A: Chemical, 229(1-2):151-158.

Zhou, C.H. et al. (2008) "Chemoselective catalytic conversion of glycerol as a biorenewable source to valuable commodity chemicals," 37(3):527-549.

METHODS OF CONVERTING POLYOLS

CROSS-REFERENCE

This application is a Continuation of International Application No. PCT/US2013/28618, filed Mar. 1, 2013, which claims the benefit of U.S. Provisional Application No. 61/606,103, filed Mar. 2, 2012, both of which applications are incorporated herein by reference in their entirety.

STATEMENT AS TO FEDERALLY SPONSORED RESEARCH

This invention was made with government support under CHE-0650456 NSF, CHE-1205189, and an ACC fellowship (CHE-0836095) awarded by the National Science Foundation. The government has certain rights in the invention.

BACKGROUND OF THE INVENTION

The use of biomass and biomass-derived feedstocks in the production of fine and commodity chemicals is hindered by the lack of cost effective purification and conversion processes. The development of efficient and selective catalytic transformations should allow biomass feedstocks to become economically competitive with traditional petroleum-based feedstocks. Ideally, the conversion reactions will be applicable to a range of substrates and tolerant of crude biomass inputs.

Glycerol is of particular interest as a renewable raw material, because it is currently being generated in vast quantities as a byproduct of biodiesel production. The attractiveness of glycerol as a sustainable platform chemical has inspired research efforts to use the triol as a building block for a variety of functionalized and reduced structures.

The partial hydrogenolysis of glycerol has been envisioned as a new, direct route to 1,3-propanediol (1,3-PD) for the production of polyesters, polyurethanes, and polyethers with high renewable resource content. Particularly interesting is the production of polytrimethylene ether glycol from 1,3-PD. One strategy for selective reduction of glycerol is a tandem catalytic sequence involving the dehydration of secondary alcohols followed by hydrogenation of the resulting carbonyl groups. Several competing condensation and dehydration pathways are available to glycerol in acidic aqueous medium, which typically leads to complex product profiles and low selectivity.

Efficient conversion of glycerol to higher value products will require the development of highly active, selective catalysts. It will be important to identify robust catalysts that are tolerant of water and acid at the high temperatures required for the dehydration step. For example, biodiesel production employs base catalyzed transesterification of triglycerides with methanol, which generates approximately 10% byproduct glycerol. This has flooded the glycerol market. The price of crude glycerol has dropped dramatically. Biodiesel production is expected to increase significantly in the next decade. One solution to the "glycerol glut" problem is to catalytically convert glycerol to a higher value product. Targets can include 1,3-propanediol, 1-propanol, and 2-propanol. Of the possible products, 1,3-propanediol is most valuable, having a ready application in the production of polyesters. For example, Dupont markets this polyester as Sorona®; the current commercial process for 1,3-propanediol employs fermentation of glucose using genetically engineered microorganisms. Previous reports of glycerol hydrogenolysis have employed both homogeneous and heterogeneous catalysts. Selectivity is generally poor, with a wide range of products including ethers, esters, alcohols and diols. Most reported procedures have employed organic solvents.

Early attempts to demonstrate the feasibility of selective conversion of glycerol to 1,3-PD utilized homogeneous catalysts yielding at best 21% 1,3-PD with 45% selectivity using a $Rh(CO)_2(acac)$ complex with tungstic acid ($H_2WO_4$) at 200° C. under 313 atm of $H_2$/CO. Early work with heterogeneous catalysts such as copper chromite showed selectivity for 1,2-PD, with <5% 1,3-PD. More recently, heterogeneous catalysts have been identified that show improved selectivity for 1,3-PD. With Pt on sulfonated $ZrO_2$ selectivities of up to 56% for 1,3-PD were reported.

Homogenous catalysts have a distinct advantage in that the application of mechanistic understanding can allow rational tuning of catalyst structure and reaction conditions to optimize activity, selectivity and lifetimes. Schlaf and coworkers have explored the reduction of terminal vicinal diols to n-alcohols using homogeneous Ru ionic hydrogenation catalysts and through these studies have provided insight into various factors that control deoxygenation selectivity. The use of diol models, which are less reactive than their polyol analogs, enabled kinetic analysis and more thorough characterization of product profiles. The most selective of the Ru hydrogenation catalysts was $[Cp*Ru(CO)_2(H_2)][OTf]$, which achieved a 54% yield of 1-propanol in sulfolane solvent at 110° C. and 710 psi $H_2$ using trifluoromethanesulfonic acid (HOTf) as the catalyst for the initial dehydration step. In addition to the 1-propanol hydrogenation product, the formation of several ether condensation products was observed, including significant yields of propylene glycol propyl ether (11%) and di-n-propyl ether (15%). The overall selectivity for reduction of the secondary hydroxyl group is 99%. The high regioselectivity of the ruthenium catalyst was impressive, but the catalyst is deactivated by water, which is a byproduct of the reaction. The active Ru dihydrogen complex is deprotonated by water to yield an inactive dimer. This catalyst decomposition makes it impractical for use with inherently wet glycerol from biodiesel production. Several ruthenium containing ionic hydrogenation catalysts with N-donor ligands have demonstrated greater solubility and stability in aqueous solution, however significant thermal decomposition and/or reduced selectivities were observed.

The homogeneous ruthenium systems reported to date represent significant advances in the development of selective polyol deoxygenation catalysts, demonstrating unprecedented regioselectivity in partial diol deoxygenation. In addition, studies of these systems have delineated many of the competitive equilibria and condensation pathways that are common to alcohols in acidic medium and must be minimized for effective conversion. As vicinal diol groups are common to all sugar polyols, the lessons learned using these model substrates are expected to be broadly applicable. To fully develop and optimize effective polyol deoxygenation technologies, catalysts that exhibit greater stability at high temperatures in the presence of water are needed.

Thus, there is a need for catalysts and processes that can efficiently convert polyols (e.g., glycerol) into other products, such as 1,3-propanediol as well as others.

SUMMARY OF THE INVENTION

The present invention provides catalysts and methods for converting polyols. In some aspects, the methods provided can include using a metal pincer catalyst (e.g., an iridium pincer catalyst) to remove at least one alcohol group from a polyol. In certain aspects, the methods provided can include converting glycerol to 1,3-propanediol.

In one aspect, the present invention includes a method for removing at least one alcohol group from a polyol, the method including reacting a polyol, hydrogen ($H_2$) gas, an acid, an organic solvent, and a metal pincer catalyst to form a reaction product, the polyol having at least two alcohol groups and the reaction product including the polyol having at least one fewer alcohol groups, and wherein the metal pincer catalyst has the general formula (I):

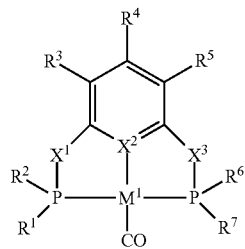

wherein $M^1$ is iridium or rhodium, wherein each of $X^1$ and $X^3$ are independently selected from C or O, wherein $X^2$ is C or N, and wherein each of $R^1$, $R^2$, $R^3$, $R^4$, $R^5$, $R^6$, and $R^7$ are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, the reacting is carried out at a temperature greater than about 160° C. In certain embodiments, the polyol includes a linear or cyclic $C_1$-$C_6$ alkane molecule substituted with the at least two alcohol groups. In some embodiments, the acid includes a homogeneous or heterogeneous proton donor. In certain embodiments, the acid can include sulfuric acid, tungstic acid, phosphoric acid, hydrochloric acid and/or trifluoromethanesulfonic acid. In some embodiments, the homogeneous acid can be used at a concentration range of about 0.03M to about 0.1M. In certain embodiments, the organic solvent includes dioxane, sulfolane, 1,3-dimethyl-2-imidazolidinone, 1-methyl-2-pyrrolidone, 1-methyl-2-piperidone, and/or bis(2-methoxyethyl)ether. In some embodiments, $M^1$ is iridium. In certain embodiments, $M^1$ is rhodium. In some embodiments, $X^1$ and $X^3$ are O. In certain embodiments, $X^2$ is C. In some embodiments, $R^1$, $R^2$, $R^6$ and $R^7$ are the same. In certain embodiments, at least one of $R^3$, $R^4$ or $R^5$ can include a linking group. In some embodiments, the linking group can be coupled to a solid support. In certain embodiments, the reacting can be carried out between about 160° C. to about 220° C. In some embodiments, the reacting can be carried out between about 170° C. to about 200° C. In certain embodiments, the polyol is glycerol and the reaction product comprises 1,3-propanediol. In some embodiments, greater than about 60% of the glycerol is converted to 1,3-propanediol. In certain embodiments, the reaction product can further include 1-propanol. In some embodiments, the polyol can include 1,2-propanediol and the reaction product can include 1-propanol. In some embodiments, the metal pincer catalyst can be present at about 0.05 to about 1 mole % with respect to the polyol. In certain embodiments, the polyol is glycerol and, before the reacting, the method further includes combining crude glycerol byproduct from transesterification of triglycerides with an acid to form a separated mixture comprising a crude product separated from a solution including glycerol, methanol, and methyl ester.

In another aspect, the present invention includes a method for removing at least one alcohol group from a polyol, the method including reacting a polyol, hydrogen ($H_2$) gas, an acid, an organic solvent, and a metal pincer catalyst to form a reaction product, the polyol having at least two alcohol groups and the reaction product including the polyol having at least one fewer alcohol groups, and wherein the metal pincer catalyst has the general formula (II):

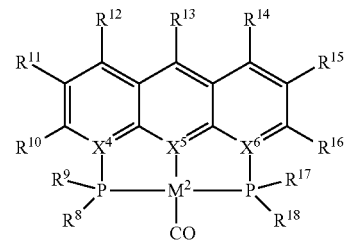

wherein $M^2$ is iridium or rhodium, wherein each of $X^4$, $X^5$ and $X^6$ are independently selected from C or N, and wherein each of $R^8$, $R^9$, $R^{10}$, $R^{11}$, $R^{12}$, $R^{13}$, $R^{14}$, $R^{15}$, $R^{16}$, $R^{17}$ and $R^{18}$, are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, the reacting can be carried out at a temperature greater than about 160° C. In certain embodiments, the polyol includes a linear or cyclic $C_1$-$C_6$ alkane molecule substituted with the at least two alcohol groups. In some embodiments, the acid includes a homogeneous or heterogeneous proton donor. In certain embodiments, the acid can include sulfuric acid, tungstic acid, phosphoric acid, hydrochloric acid and/or trifluoromethanesulfonic acid. In some embodiments, the homogeneous acid can be used at a concentration range of about 0.03M to about 0.1M. In certain embodiments, the organic solvent includes dioxane, sulfolane, 1,3-dimethyl-2-imidazolidinone, 1-methyl-2-pyrrolidone, 1-methyl-2-piperidone, and/or bis(2-methoxyethyl)ether. In some embodiments, $M^2$ is iridium. In certain embodiments, $M^2$ is rhodium. In some embodiments, $X^4$, $X^5$ and $X^6$ are C. In some embodiments, $R^8$, $R^9$, $R^{17}$ and $R^{18}$ are the same. In certain embodiments, at least one of $R^{11}$, $R^{12}$, $R^{13}$, $R^{14}$, or $R^{15}$ can include a linking group. In some embodiments, the linking group can be coupled to a solid support. In certain embodiments, the reacting can be carried out between about 160° C. to about 220° C. In some embodiments, the reacting can be carried out between about 170° C. to about 200° C. In certain embodiments, the polyol is glycerol and the reaction product comprises 1,3-propanediol. In some embodiments, greater than about 60% of the glycerol is converted to 1,3-propanediol. In certain embodiments, the reaction product can further include 1-propanol. In some embodiments, the polyol can include 1,2-propanediol and the reaction product can include 1-propanol. In some embodiments, the metal pincer catalyst can be present at about 0.05 to about 1 mole % with respect to the polyol. In certain embodiments, the polyol is glycerol and, before the reacting, the method further includes combining crude glycerol byproduct from transesterification of triglycerides with an acid to form a separated mixture comprising a crude product separated from a solution including glycerol, methanol, and methyl ester.

In yet another aspect, the present invention includes a method for removing at least one alcohol group from a polyol, the method including reacting a polyol, hydrogen ($H_2$) gas, an acid, an organic solvent, and a metal pincer catalyst to form a reaction product, the polyol having at least two alcohol groups and the reaction product including the polyol having at least one fewer alcohol groups, and wherein the metal pincer catalyst has the general formula (III):

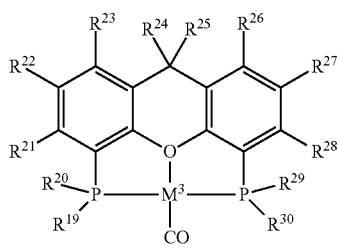

wherein $M^3$ is iridium or rhodium, and wherein each of $R^{19}$, $R^{20}$, $R^{21}$, $R^{22}$, $R^{23}$, $R^{24}$, $R^{25}$, $R^{26}$, $R^{27}$, $R^{28}$, $R^{29}$ and $R^{30}$ are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, the reacting can be carried out at a temperature greater than about 160° C. In certain embodiments, the polyol includes a linear or cyclic $C_1$-$C_6$ alkane molecule substituted with the at least two alcohol groups. In some embodiments, the acid includes a homogeneous or heterogeneous proton donor. In certain embodiments, the acid can include sulfuric acid, tungstic acid, phosphoric acid, hydrochloric acid and/or trifluoromethanesulfonic acid. In some embodiments, the homogeneous acid can be used at a concentration range of about 0.03M to about 0.1M. In certain embodiments, the organic solvent includes dioxane, sulfolane, 1,3-dimethyl-2-imidazolidinone, 1-methyl-2-pyrrolidone, 1-methyl-2-piperidone, and/or bis(2-methoxyethyl)ether. In some embodiments, $M^3$ is iridium. In certain embodiments, $M^3$ is rhodium. In some embodiments, $R^{19}$, $R^{20}$, $R^{29}$ and $R^{30}$ are the same. In certain embodiments, at least one of $R^{22}$, $R^{23}$, $R^{24}$, $R^{25}$, $R^{26}$ or $R^{27}$ can include a linking group. In some embodiments, the linking group can be coupled to a solid support. In certain embodiments, the reacting can be carried out between about 160° C. to about 220° C. In some embodiments, the reacting can be carried out between about 170° C. to about 200° C. In certain embodiments, the polyol is glycerol and the reaction product comprises 1,3-propanediol. In some embodiments, greater than about 60% of the glycerol is converted to 1,3-propanediol. In certain embodiments, the reaction product can further include 1-propanol. In some embodiments, the polyol can include 1,2-propanediol and the reaction product can include 1-propanol. In some embodiments, the metal pincer catalyst can be present at about 0.05 to about 1 mole % with respect to the polyol. In certain embodiments, the polyol is glycerol and, before the reacting, the method further includes combining crude glycerol byproduct from transesterification of triglycerides with an acid to form a separated mixture comprising a crude product separated from a solution including glycerol, methanol, and methyl ester.

In yet another aspect, the present invention includes a method for removing at least one alcohol group from a polyol, the method including reacting a polyol, hydrogen ($H_2$) gas, an acid, an organic solvent, and a metal pincer catalyst to form a reaction product, the polyol having at least two alcohol groups and the reaction product including the polyol having at least one fewer alcohol groups, and wherein the metal pincer catalyst has the general formula (IV):

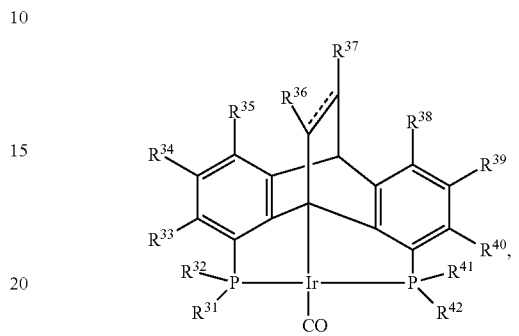

wherein each of $R^{31}$, $R^{32}$, $R^{33}$, $R^{34}$, $R^{35}$, $R^{38}$, $R^{39}$, $R^{40}$, $R^{41}$, and $R^{42}$ are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; wherein ====== is a single or double bond; and wherein each of $R^{36}$ and $R^{37}$ are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, or wherein $R^{36}$ and $R^{37}$ are joined together to form a substituted or unsubstituted cycloalkyl, substituted or unsubstituted heterocycloalkyl, substituted or unsubstituted aryl, or substituted or unsubstituted heteroaryl. In some embodiments, the reacting can be carried out at a temperature greater than about 160° C. In certain embodiments, the polyol includes a linear or cyclic $C_1$-$C_6$ alkane molecule substituted with the at least two alcohol groups. In some embodiments, the acid includes a homogeneous or heterogeneous proton donor. In certain embodiments, the acid can include sulfuric acid, tungstic acid, phosphoric acid, hydrochloric acid and/or trifluoromethanesulfonic acid. In some embodiments, the homogeneous acid can be used at a concentration range of about 0.03M to about 0.1M. In certain embodiments, the organic solvent includes dioxane, sulfolane, 1,3-dimethyl-2-imidazolidinone, 1-methyl-2-pyrrolidone, 1-methyl-2-piperidone, and/or bis(2-methoxyethyl)ether. In some embodiments, $R^{31}$, $R^{32}$, $R^{41}$ and $R^{42}$ are the same. In certain embodiments, at least one of $R^{33}$, $R^{34}$, $R^{35}$, $R^{36}$, $R^{37}$, $R^{38}$, $R^{39}$, or $R^{40}$ comprises a linking group. In some embodiments, the linking group can be coupled to a solid support. In certain embodiments, the reacting can be carried out between about 160° C. to about 220° C. In some embodiments, the reacting can be carried out between about 170° C. to about 200° C. In certain embodiments, the polyol is glycerol and the reaction product comprises 1,3-propanediol. In some embodiments, greater than about 60% of the glycerol is converted to 1,3-propanediol. In certain embodiments, the reaction product can further include 1-propanol. In some embodiments, the polyol can include 1,2-propanediol and the reaction product can include 1-propanol. In some embodiments, the metal pincer catalyst can be present at about 0.05 to about 1 mole % with respect to the polyol. In certain embodiments, the polyol is glycerol and, before the reacting, the method further includes combining crude glycerol byproduct from transesterification of triglycerides with an acid to form a separated mixture comprising a crude product separated from a solution including glycerol, methanol, and methyl ester.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
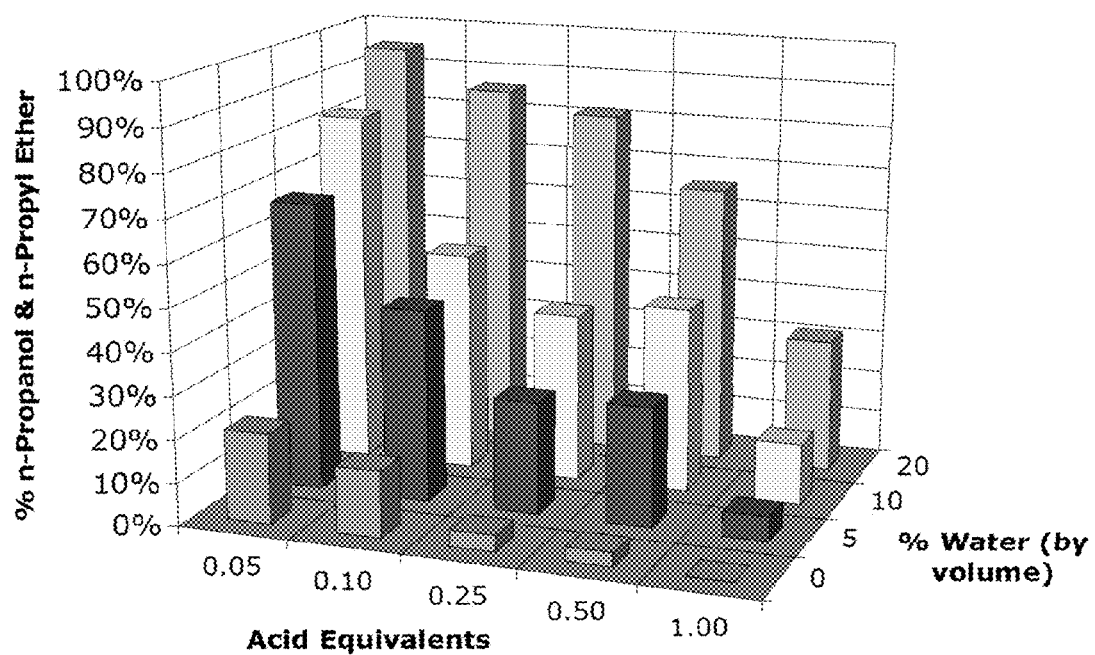
FIG. 1 shows the yield of (1-propanol+n-propyl ether) in the deoxygenation of 1,2-PD as a function of [acid]/[1,2-PD]o) and % water by volume. n-propyl ether yield was <9% in all reactions.

The present invention provides catalysts and methods for converting polyols. In some aspects, the methods provided can include using a metal pincer catalyst (e.g., an iridium pincer catalyst) to remove at least one alcohol group from a polyol. In certain aspects, the methods provided can include converting glycerol to 1,3-propanediol.

As will be described further herein, the present invention is based at least in-part on the surprising discovery that a metal pincer catalyst (e.g., an iridium pincer catalyst) can be used, e.g., to remove alcohols from polyols. In one aspect, the present invention is based at least in-part on the discovery that a Ir(I) carbonyl pre-catalyst is water and air-stable and can be used to catalyze hydrogenolysis of polyols (e.g., to convert glycerol to 1,3-propanediol). Additional aspects about the present invention further include the discovery that the catalysts described herein can be used a low concentrations (e.g., less than 1 mole percent) to efficiently and selectively catalyze hydrogenolysis of polyols (e.g., to convert glycerol to 1,3-propanediol).

As used herein, the term "alkyl" refers to a straight or branched, saturated, aliphatic radical having the number of carbon atoms indicated. For example, C$_1$-C$_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together. As used herein, the term "heteroalkyl" refers to a straight or branched, saturated, aliphatic radical of carbon atoms, where at least one of the carbon atoms is replaced with a heteroatom, such as N, O or S. Additional heteroatoms can also be useful, including, but not limited to, B, Al, Si and P.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —(CH$_2$)$_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

The groups described herein can be substituted or unsubstituted. Substituents can include any group described herein. For example, substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups, such as alkyl, aryl, cyano (CN), amino, sulfide, aldehyde, ester, ether, acid, hydroxyl or halide. Substituents can be a reactive group, such as but not limited to chloro, bromo, iodo, hydroxyl, or amino. Suitable substituents can be selected from: —OR', =O, =NR', =N—OR', —NR'R", —SR', -halogen, —SiR'R"R''', —OC(O)R', —C(O)R', —CO$_2$R', —CONR'R", —OC(O)NR'R", —NR'R"R'''Cl, —NR"C(O)R', —NR'—C(O)NR"R''', —NR"C(O)$_2$R', —NH—C(NH$_2$)=NH, —NR'C(NH$_2$) =NH, —NH—C(NH$_2$)=NR', —S(O)R', —S(O)$_2$R', —S(O)$_2$NR'R", —SO$_3$R', —SO$_3$Na, —SO$_3$K, —SO$_3$H, —PO$_3$Na$_2$, —PO$_3$H$_2$, —PO(OR')$_2$, —PO(OR')R", (—CN and —NO$_2$ in a number ranging from zero to (2m'+1), where m' is the total number of carbon atoms in such radical. R', R" and R''' each independently refer to hydrogen, unsubstituted (C$_1$-C$_8$)alkyl and heteroalkyl, unsubstituted aryl, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O) CF$_3$, —C(O)CH$_2$OCH$_3$, and the like).

As used herein, the term "alkoxy" refers to an alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

As used herein, the term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene.

As used herein, the term "alkyl amine" refers to an alkyl groups as defined within, having one or more amino groups. The amino groups can be primary, secondary or tertiary. The alkyl amine can be further substituted with a hydroxy group. Alkyl amines can include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

As used herein, the term "halogen" or "halide" refers to fluorine, chlorine, bromine and iodine. As used herein, the term "haloalkyl" refers to alkyl as defined above where some or all of the hydrogen atoms are substituted with halogen atoms. Halogen (halo) preferably represents chloro or fluoro, but may also be bromo or iodo. As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, etc.

As used herein, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

As used herein, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—.

As used herein, the term "heterocycloalkylene" refers to a heterocycloalkyl group, as defined above, linking at least two other groups. The two moieties linked to the heterocycloalkylene can be linked to the same atom or different atoms of the heterocycloalkylene.

As used herein, the term "aryl" refers to a monocyclic or fused bicyclic, tricyclic or greater, aromatic ring assembly containing 6 to 16 ring carbon atoms. For example, aryl may be phenyl, benzyl, azulenyl or naphthyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Aryl groups can include, but are not limited to, naphthyl, phenyl or phenyl mono- or disubstituted by alkoxy, phenyl, halogen, alkyl or trifluoromethyl, phenyl or phenyl-mono- or disubstituted by alkoxy, halogen or trifluoromethyl, and in particular phenyl.

As used herein, the term "arylene" refers to an aryl group, as defined above, linking at least two other groups. The two moieties linked to the arylene are linked to different atoms of the arylene. Arylene groups include, but are not limited to, phenylene.

As used herein, the terms "alkoxy-aryl" or "aryloxy" refers to an aryl group, as defined above, where one of the moieties linked to the aryl is linked through an oxygen atom. Alkoxy-aryl groups include, but are not limited to, phenoxy ($C_6H_5O$—). The present invention also includes alkoxy-heteroaryl or heteroaryloxy groups.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Suitable groups for the present invention can also include heteroarylene and heteroarylene-oxy groups similar to the description above for arylene and arylene-oxy groups.

Similarly, aryl and heteroaryl groups described herein can be substituted or unsubstituted. Substituents can include any group described herein. For example, substituents for the aryl and heteroaryl groups are varied, such as alkyl, aryl, CN, amino, sulfide, aldehyde, ester, ether, acid, hydroxyl or halide. Substituents can be a reactive group, such as but not limited to chloro, bromo, iodo, hydroxyl, or amino. Substituents can be selected from: -halogen, —OR', —OC(O)R', —NR'R", —SR', —R', —CN, —NO$_2$, —CO$_2$R', —CONR'R", —C(O)R', —OC(O)NR'R", —NR'R"R'"Cl, —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —SO$_3$R', —SO$_3$Na, —SO$_3$K, —SO$_3$H, —PO$_3$Na$_2$, —PO$_3$H$_2$, —PO(OR')$_2$, —PO(OR')R", —N$_3$, —CH(Ph)$_2$, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl. The present invention also includes alkyl-heteroaryl groups.

As used herein, the term "alkenyl-aryl" refers to a radical having both an alkenyl component and an aryl component, where the alkenyl component links the aryl component to the point of attachment. The alkenyl component is as defined above, except that the alkenyl component is at least divalent in order to link to the aryl component and to the point of attachment. The aryl component is as defined above. Examples of alkenyl-aryl include ethenyl-phenyl, among others. The present invention also includes alkenyl-heteroaryl groups.

As used herein, the term "alkynyl-aryl" refers to a radical having both an alkynyl component and a aryl component, where the alkynyl component links the aryl component to the point of attachment. The alkynyl component is as defined above, except that the alkynyl component is at least divalent in order to link to the aryl component and to the point of attachment. The aryl component is as defined above. Examples of alkynyl-aryl include ethynyl-phenyl, among others. The present invention also includes alkynyl-heteroaryl groups.

In one aspect, the present invention includes methods converting polyols. In one embodiment, the present invention includes a method for removing at least one alcohol group from a polyol. The method can include, e.g., reacting a polyol, hydrogen (H$_2$) gas, an acid, an organic solvent, and a metal pincer catalyst to form a reaction product, the polyol having at least two alcohol groups and the reaction product including the polyol having at least one fewer alcohol groups.

In the present description, any concentration range, percentage range, ratio range, or integer range is to be understood to include the value of any integer within the recited range and, when appropriate, fractions thereof, unless otherwise indicated. As used herein, the term "about" means±20% the indicated value, range or structure, unless otherwise indicated.

The catalysts and methods of the present invention can be used in converting a variety of polyol compounds. As used herein, the term "polyol" can refer to, e.g., molecules having at least two alcohol groups. In some embodiments, the polyols can include linear or cyclic alkanes. The linear or cyclic alkane molecules can be substituted with an alcohol group, e.g., at least two alcohol groups. The alkanes, e.g., including at least two alcohol groups, can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. In certain embodiments, the polyols can include linear or cyclic C$_1$-C$_6$ alkanes. In some embodiments, the polyols can include more than two alcohol groups, such as at least three alcohol groups, at least four alcohol groups, and at least five alcohol groups. Suitable polyols can include, but are not limited to, glycerol, erythritol, xylitol, sorbitol, mannitol, glucose, fructose, or sucrose. In one embodiment, the polyols can include glycerol. In another embodiment, the polyols can include 1,3-propanediol.

Hydrogen gas can be provided for the methods herein by myriad ways. In some embodiments, hydrogen gas alone can be provided before, during and/or after combining and/or reacting various constituents described further herein. In certain embodiments, hydrogen gas may be mixed with other gases. For example, syngas (or synthesis gas), which includes a mixture of hydrogen gas and carbon monoxide, can be used. Gases including hydrogen gas can be provided (e.g., bubbled in a reaction vessel) at a variety of pressures. Suitable pressures can be tailored according to desired reaction conditions, e.g., to optimize conversion efficiency. Example pressures can include, but are not limited to, between about 1000 psi to about 1500 psi, between about 1100 psi to about 1400 psi, or between about 1200 psi to about 1300 psi.

The methods of the present invention can further include using an acid to facilitate conversion of a polyol (e.g., glycerol). Suitable acids can include homogeneous or heterogeneous proton donors, such as, but not limited to, sulfuric acid, tungstic acid, phosphoric acid, hydrochloric acid and/or trifluoromethanesulfonic acid. The acids can be used a variety of concentrations. In some embodiments, the acid can be present at concentrations ranging, e.g., between about 0.03M to about 0.1M, between about 0.04M to about 0.1M, between 0.05M to about 0.1M, between about 0.06M to about 0.1M, between about 0.07M to about 0.1M, between about 0.08M to about 0.1M, and between about 0.09M to about 0.1M. The pH provided by the acid can be around a pH of 1.

The conversion reactions can be carried out in an organic solvent. In some embodiments, a polyol, a hydrogen gas, an acid, a metal pincer catalyst, and the organic solvent can be combined and heated to a desired temperature to carry out a conversion reaction of the polyol. The various components used in the reactions can be combined in a variety of ways that will be generally understood by one of ordinary skill in the art. In certain embodiments, polar aprotic solvents with high boiling points can be used. Some example organic solvents can include, but are not limited to, dioxane, sulfolane, 1,3-dimethyl-2-imidazolidinone, 1-methyl-2-pyrrolidone, 1-methyl-2-piperidone, and/or bis(2-methoxyethyl)ether (or diglyme). In some embodiments, the organic solvent can be used to solubilize glycerol. In certain embodiments, water can be added before, during or after the reaction. Hydrogenolysis of the polyol (e.g., glycerol) also forms water as a product of the conversion reaction.

A variety of catalysts (e.g., metal pincer catalysts) can be used. In one embodiment, the present invention includes a metal pincer catalyst having the general formula (I):

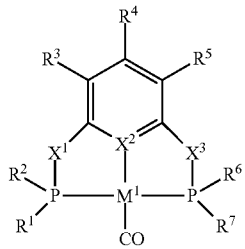

wherein $M^1$ is iridium or rhodium, wherein each of $X^1$ and $X^3$ are independently selected from C or O, wherein $X^2$ is C or N, and wherein each of $R^1$, $R^2$, $R^3$, $R^4$, $R^5$, $R^6$, and $R^7$ are independently selected from the group consisting of hydrogen, a halide, —OH, —NH$_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $M^1$ is iridium. In certain embodiments, $X^1$ and $X^3$ are O. In some embodiments, $X^2$ is carbon. In certain embodiments, $R^1$, $R^2$, $R^6$ and $R^7$ are the same. In some embodiments, $R^1$, $R^2$, $R^6$ and $R^7$ are the same and selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^1$, $R^2$, $R^6$ and $R^7$ are the same and are substituted or unsubstituted alkyl (e.g., $C_1$-$C_6$ alkyl). The present invention further includes any acceptable salts of general formula (I).

In another embodiment, the present invention includes a metal pincer catalyst having the general formula (Ia):

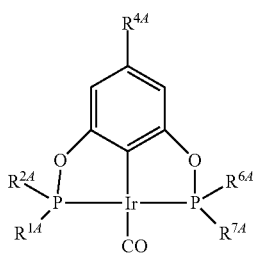

wherein each of $R^{1A}$, $R^{2A}$, $R^{4A}$, $R^{6A}$, and $R^{7A}$ are independently selected from the group consisting of hydrogen, a halide, —OH, —NH$_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In certain embodiments, $R^{1A}$, $R^{2A}$, $R^{6A}$, and $R^{7A}$ are the same. In some embodiments, $R^{1A}$, $R^{2A}$, $R^{6A}$, and $R^{7A}$ are the same and selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{1A}$, $R^{2A}$, $R^{6A}$, and $R^{7A}$ are the same and are substituted or unsubstituted alkyl (e.g., $C_1$-$C_6$ alkyl). The present invention further includes any acceptable salts of general formula (Ia).

In yet another embodiment, the present invention includes a metal pincer catalyst having the general formula (II):

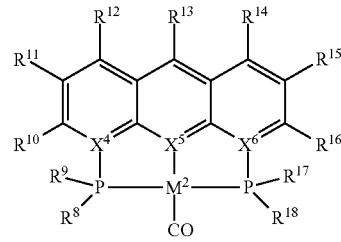

wherein $M^2$ is iridium or rhodium, wherein each of $X^4$, $X^5$ and $X^6$ are independently selected from C or N, and wherein each of $R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from the group consisting of hydrogen, a halide, —OH, —NH$_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $M^2$ is iridium. In certain embodiments, $X^4$, $X^5$, and $X^6$ are carbon. In certain embodiments, $R^8$, $R^9$, $R^{17}$ and $R^{18}$ are the same. In some embodiments, $R^8$, $R^9$, $R^{17}$ and $R^{18}$ are the same and selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^8$, $R^9$, $R^{17}$ and $R^{18}$ are the same and are substituted or unsubstituted alkyl (e.g., $C_1$-$C_6$ alkyl). The present invention further includes any acceptable salts of general formula (II).

In yet another embodiment, the present invention includes a metal pincer catalyst having the general formula (IIa):

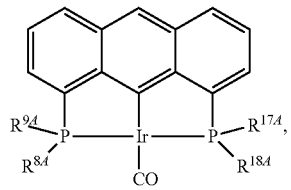

wherein each of $R^{8A}$, $R^{9A}$, $R^{17A}$, and $R^{18A}$ are independently selected from the group consisting of hydrogen, a halide, —OH, —NH$_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In certain embodiments, $R^{8A}$, $R^{9A}$, $R^{17A}$, and $R^{18A}$ are the same. In some embodiments, $R^{8A}$, $R^{9A}$, $R^{17A}$, and $R^{18A}$ are the same and selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{8A}$, $R^{9A}$, $R^{17A}$, and $R^{18A}$ are the same and are substituted or unsubstituted alkyl (e.g., $C_1$-$C_6$ alkyl). The present invention further includes any acceptable salts of general formula (IIa).

In yet another embodiment, the present invention includes a metal pincer catalyst having the general formula (III):

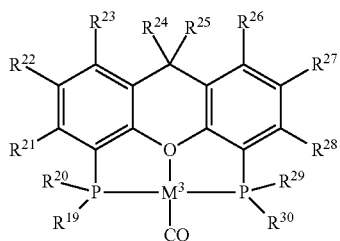

wherein $M^3$ is iridium or rhodium, and wherein each of $R^{19}$, $R^{20}$, $R^{21}$, $R^{22}$, $R^{23}$, $R^{24}$, $R^{25}$, $R^{26}$, $R^{27}$, $R^{28}$, $R^{29}$ and $R^{30}$ are independently selected from the group consisting of hydrogen, a halide, —OH, —NH$_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $M^3$ is iridium. In certain embodiments, $R^{19}$, $R^{20}$, $R^{29}$ and $R^{30}$ are the same. In some embodiments, $R^{19}$, $R^{20}$, $R^{29}$ and $R^{30}$ are the same and selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{19}$, $R^{20}$, $R^{29}$ and $R^{30}$ are the same and are substituted or unsubstituted alkyl (e.g., $C_1$-$C_6$ alkyl). The present invention further includes any acceptable salts of general formula (III).

In yet another embodiment, the present invention includes a metal pincer catalyst having the general formula (IIIa):

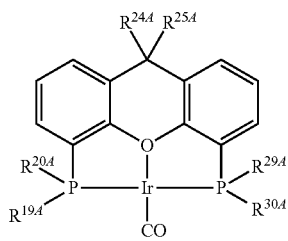

wherein each of $R^{19A}$, $R^{20A}$, $R^{24A}$, $R^{25A}$, $R^{29A}$, and $R^{30A}$ are independently selected from the group consisting of hydrogen, a halide, —OH, —NH$_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In certain embodiments, $R^{19A}$, $R^{20A}$, $R^{29A}$, and $R^{30A}$ are the same. In some embodiments, $R^{19A}$, $R^{20A}$, $R^{29A}$, and $R^{30A}$ are the same and selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{19A}$, $R^{20A}$, $R^{29A}$, and $R^{30A}$ are the same and are substituted or unsubstituted alkyl (e.g., $C_1$-$C_6$ alkyl). The present invention further includes any acceptable salts of general formula (Ma).

In some embodiments, the catalysts used in the present invention can include triptycene catalysts. For example, the present invention includes a catalyst having the general formula (IV):

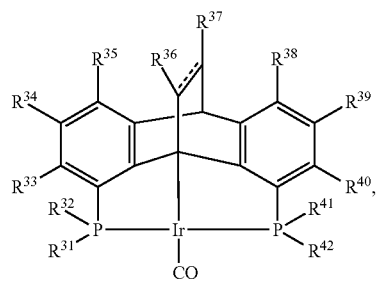

wherein each of $R^{31}$, $R^{32}$, $R^{33}$, $R^{34}$, $R^{35}$, $R^{38}$, $R^{39}$, $R^{40}$, $R^{41}$, and $R^{42}$ are independently selected from the group consisting of hydrogen, a halide, —OH, —NH$_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; wherein ====== is a single or double bond, and wherein each of $R^{36}$ and $R^{37}$ are independently selected from the group consisting of hydrogen, a halide, —OH, —NH$_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, or wherein $R^{36}$ and $R^{37}$ are joined together to form a substituted or unsubstituted cycloalkyl, substituted or unsubstituted heterocycloalkyl, substituted or unsubstituted aryl, or substituted or unsubstituted heteroaryl. In certain embodiments, ====== is a single bond. In some embodiments, ====== is a double bond. In certain embodiments, $R^{31}$, $R^{32}$, $R^{41}$, and $R^{42}$ are the same. In some embodiments, $R^{31}$, $R^{32}$, $R^{41}$, and $R^{42}$ are the same and selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{31}$, $R^{32}$, $R^{41}$, and $R^{42}$ are the same and are substituted or unsubstituted alkyl (e.g., $C_1$-$C_6$ alkyl). The present invention further includes any acceptable salts of general formula (IV).

In yet another embodiment, the present invention includes a metal pincer catalyst having the general formula (IVa):

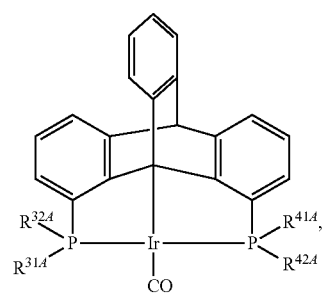

wherein each of $R^{31A}$, $R^{32A}$, $R^{41A}$, and $R^{42A}$ are independently selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In certain embodiments, $R^{31A}$, $R^{32A}$, $R^{41A}$, and $R^{42A}$ are the same. In some embodiments, $R^{31A}$, $R^{32A}$, $R^{41A}$, and $R^{42A}$ are the same and are substituted or unsubstituted alkyl (e.g., $C_1$-$C_6$ alkyl). The present invention further includes any acceptable salts of general formula (IVa).

In yet another embodiment, the present invention includes a metal pincer catalyst having the general formula (IVb):

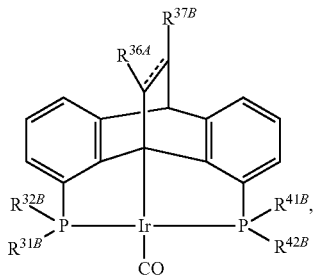

wherein each of $R^{31B}$, $R^{32B}$, $R^{36B}$, $R^{37B}$, $R^{41B}$, and $R^{42B}$ are independently selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In certain embodiments, $R^{31A}$, $R^{32A}$, $R^{41A}$, and $R^{42A}$ are the same. The symbol ====== can be a single bond or double bond. In certain embodiments, ====== is a single bond. In some embodiments, ====== is a double bond. In some embodiments, $R^{36B}$ and $R^{37B}$ can be joined together to form a substituted or unsubstituted cycloalkyl, substituted or unsubstituted heterocycloalkyl, substituted or unsubstituted aryl, or substituted or unsubstituted heteroaryl. In some embodiments, $R^{31B}$, $R^{32B}$, $R^{41B}$, and $R^{42B}$ are the same and are substituted or unsubstituted alkyl (e.g., $C_1$-$C_6$ alkyl). The present invention further includes any acceptable salts of general formula (IVb).

One surprising aspect regarding the present invention includes the low concentration of catalyst needed to produce a reaction product (e.g., 1,3-propanediol). For example, the catalyst can be present at a concentration of less than about 1 mole percent, less than about 0.75 mole percent, less than about 0.5 mole percent, less than about 0.25 mole percent, less than about 0.1 mole percent, or less than about 0.075 mole percent. In some embodiments, the catalyst can be present over a variety of concentration ranges, such as, but not limited to, between about 0.05 mole percent to about 1 mole percent, between about 0.1 mole percent to about 1 mole percent, between about 0.25 mole percent to about 1 mole percent, between about 0.5 mole percent to about 1 mole percent, or between about 0.75 mole percent to about 1 mole percent. Higher and lower mole percentages can be used and tailored for desired reaction conditions.

The catalysts provided herein are available commercially or may be synthesized according to methods known in the art. See, e.g., Choi, J.; MacArthur, A. H. R.; Brookhart, M.; Goldman, A. S.; Chem. Rev. 2011, 111, 1761; Albrecht, M.; Lindner, M. M.; Dalton Trans. 2011, 40, 8733; Organometallic Pincer Chemistry; Koten, G. V., Milstein, D., Eds.; Springer: Heidelberg, 2013; The Chemistry of Pincer Compounds; Morales-Morales, D., Jensen, C., Eds.; Elsevier: Amsterdam, 2007, each of which is incorporated by reference herein in their entireties.

The methods of the present invention can be carried out at a variety of temperatures. While not being limited to any particular temperature, in some embodiments, the methods can be carried out (e.g., the constituents can be reacted) at a temperature greater than about greater than about 160° C., greater than about 170° C., greater than about 180° C., greater than about 190° C., greater than about 200° C., greater than about 210° C., or greater than about 220° C. In certain embodiments, the methods can be carried out at a range of temperatures between about 100° C. and about 220° C., between about 160° C. and about 220° C., between about 170° C. and about 210° C., between about 170° C. and about 200° C., between about 180° C. and about 200° C., between about 170° C. and about 180° C., between about 180° C. and about 220° C., or between about 170° C. and about 220° C.

In one embodiment, the present invention includes methods for converting glycerol to 1,3-propanediol. The methods can include, e.g., reacting glycerol, hydrogen (H2) gas, an acid, an organic solvent, and a metal pincer catalyst to form 1,3-propanediol. The various catalysts, acids, organic solvents, and temperatures can be tailored to optimize catalysis of glycerol to form 1,3-propanediol. In some embodiments, greater than about 60% of the glycerol can be converted to 1,3-propanediol, greater than about 50% of the glycerol can be converted to 1,3-propanediol, greater than about 40% of the glycerol can be converted to 1,3-propanediol, greater than about 30% of the glycerol can be converted to 1,3-propanediol, or greater than about 20% of the glycerol can be converted to 1,3-propanediol. In certain embodiments, between about 30% and about 60% of the glycerol can be converted to 1,3-propanediol, between about 40% and about 60% of the glycerol can be converted to 1,3-propanediol, or between about 50% and about 60% of the glycerol can be converted to 1,3-propanediol.

The catalysts provided herein (e.g., the metal pincer catalysts of general formula (I), (II), (III), or (IV)) can be homogeneous or heterogeneous catalysts. In some embodiments, a reaction vessel can include both homogeneous or heterogeneous catalysts. For heterogeneous catalysts, the catalysts can be immobilized on a solid support in a variety of ways. In certain embodiments, the catalysts can be immobilized by covalent and/or noncovalent interaction with a solid support. In some embodiments, linking groups can be used to covalently attach the catalysts to solid supports. Suitable linking groups and methods of covalent attachment are generally well known in the art. Suitable solid supports can include, but are not limited to, silica, silicon, Merrifield resin, γ-alumina or polymer-based solid supports. In some embodiments, catalysts with ligands containing pendant —Si(OMe)$_3$ or —Si(Me)$_2$OMe substitution can be covalently bonded to silica via heating. Merrifield resins can contain chlorobenzyl moieties. In certain embodiments, catalysts with nucleophilic substituents in the ligand backbone (e.g. phenoxide) can be linked to the support, e.g., via an SN2 reaction. In some embodiments, with the Lewis acidity of γ-alumina, catalysts with ligands containing Lewis basic substitution (e.g. —N(CH$_3$)$_2$, —OCH$_3$, —O—K+, —OP(t-Bu)$_2$) can be adsorbed onto the support. Suitable reactions and linking groups for solid supports can also be found, e.g., in Huang, Z.; Rolfe, E.; Carson, E. C.; Brookhart, M.; Goldman, A. S.; El-Khalafy, S. H.; MacArthur, A. H. R; Adv. Synth. Catal. 2012, 352, 125; Huang, Z.; Brookhart, M.; Goldman, A. S.; Kundu, S.; Ray, A.; Scott, S. L.; Vicente, B. C.; Adv. Synth. Catal. 2009, 351, 188; Vicente, B. C.; Huang, Z.; Brookhart, M.; Goldman, A. S.; Scott, S. L.; Dalton Trans. 2011, 40, 4268; Choi, J.; MacArthur, A. H. R.; Brookhart, M.; Goldman, A. S.; Chem. Rev. 2011, 111, 1761, each of which is incorporated by reference herein in their entireties Another aspect of the present invention includes a surprising discovery that crude glycerol byproduct from transesterification of triglycerides produced during biodiesel production can be simply separated using addition of acid (e.g., sulfuric acid). Accordingly, crude glycerol byproduct can be processed before catalysis to provide a more pure form of glycerol for conversion. Surprisingly, when acid is added to the crude glycerol byproduct the crude material separates from the rest of the solution, thereby forming a separated mixture including a solution having glycerol, methanol and methyl ester. In some embodiments, the methods can include, before catalysis, combining an acid (e.g., sulfuric acid) and crude glycerol byproduct from the transesterification of triglycerides to form a separated mixture including a crude product separated from a solution including glycerol, methanol and methyl ester. The solution including glycerol, methanol and methyl ester can be extracted and used in the methods described herein, e.g., to produce 1,3-propanediol.

EXAMPLES

Example 1

At 180-220° C. under 1000-1500 psi $H_2$ gas, glycerol is converted to 1,3-propanediol in the presence of acid and an iridium catalyst. The catalyst precursor is a carbonyl complex of iridium. (Scheme A). Metal catalyst loading is 0.05-0.2 mole % with respect to glycerol. Acids can be homogeneous or heterogeneous proton donors and include any acid which will readily donate a proton to a polyol for the dehydration of that polyol. Examples of acids include but are not limited to sulfuric acid, tungstic acid, phosphoric acid, hydrochloric acid, and trifluoromethanesulfonic acid. Homogeneous acids are used at a concentration of 0.1M or pH 1. Raising the pH will increase the reaction time and decreasing the pH will decrease product selectivity. Acids that deprotonate to form anions that weakly bind to the hydrogenation catalyst are preferred. The preferred acid catalyst is sulfuric acid.

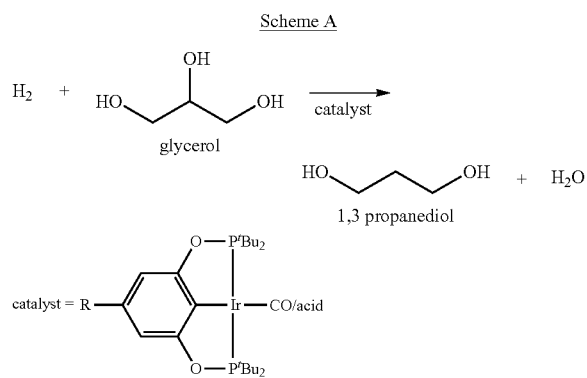

Under similar conditions, the addition of water to the reaction mixture changes the selectivity of the reaction, leading to the exclusive formation of 1-propanol. (Scheme B)

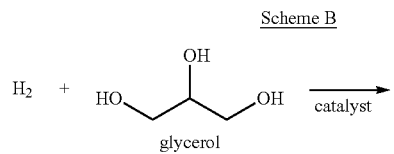

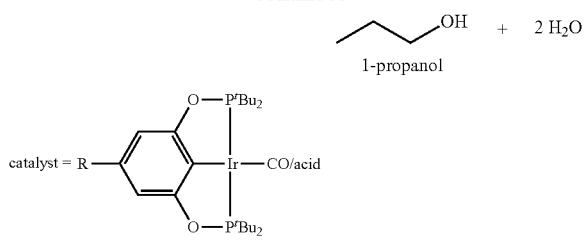

In the above, R represents a polar group appended to the para position of the phenyl ring in the ligand for the purpose of improving solubility in the highly polar reaction medium. R can be hydroxide, polyethylene glycol, an ester, a carboxylic acid.

For the examples, a Parr Multireactor 5000 was used as the high pressure reactor. It has six independent vessels made of a corrosion resistant Hastelloy C-276 alloy. Stirbar, reactants, solvents, and catalysts were added to vessels without a glass liner. Vessels were degassed by pressurizing them with 290 psi $H_2$ and purging them three times. Stir rates were set at 400 rpm. At the conclusion of reaction, vessels were cooled to room temperature, then further cooled in a dry ice/acetone bath before being vented. The $^{13}$C-NMR spectra were from the resulting neat solution. $^1$H-NMR analysis was carried out on a representative sample in $CD_3OD$.

Example 2

An Example of Conversion of Glycerol to 1-propanol

A solution of 4 grams of glycerol and 5 grams of aqueous $H_2SO_4$ (0.1M) was added to 10 mg of p-OH(POCOP)Ir(CO). The vessel was pressurized with hydrogen to 1200 psi and stirred with a Teflon coated stirbar at 400 rpm. The vessel was heated to 220° C. for 24 hrs. Pressure steadily decreased as hydrogen gas was consumed and the reaction was complete after 8 hours. After cooling, the vessel was vented and the reaction solution was analyzed by $^{13}$C-NMR spectroscopy. The product distribution was found to be 95% 1-propanol/5% 1,3-propanediol.

Example 3

An Example of Conversion of Glycerol to 1,3-propanediol 10 mg of p-OH(POCOP)Ir(CO) was added to a solution of 4 grams of glycerol and 0.10 mL concentrated $H_2SO_4$. The vessel was pressurized with hydrogen to 1200 psi and stirred with a Teflon coated stirbar at 400 rpm. The vessel was heated to 220° C. for 4 hrs. Analysis of the reaction mixture showed 50% conversion of glycerol to a 90:10 mixture of 1,3-propanediol: 1-propanol.

The range of catalysts can be explored using ligand variations including but not limited to those depicted below:

A

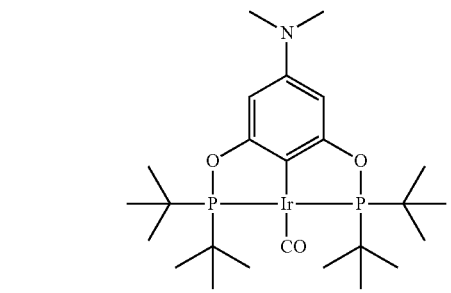

B

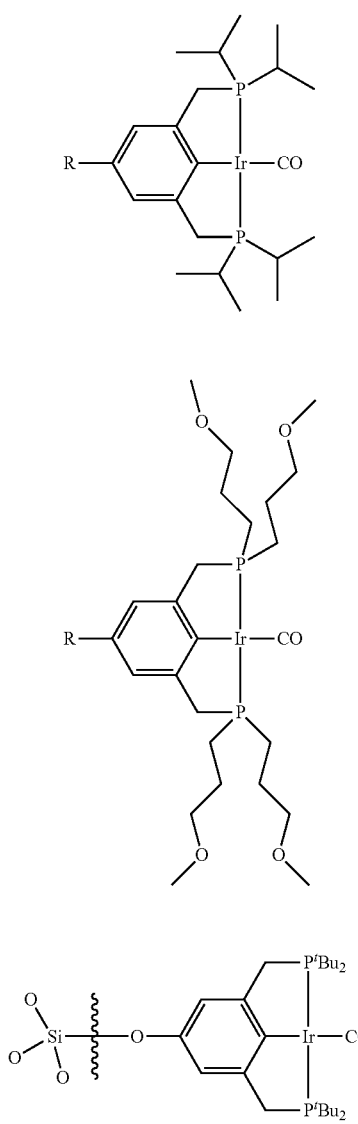

C

In A, we will reduce the steric demand of the phosphine alkyl groups. This may increase the catalytic activity. In B, we will employ methyl ether substituents on the phosphine. Related ligands have been shown to have enhanced solubility in water. In C, we plan to heterogenize the catalyst by anchoring it to a silica surface. As described further above, a variety of known techniques for linking a catalyst to a solid support can be used.

Example 4

In a typical experiment, a 30 CC Hastelloy autoclave with magnetic stirring is charged with 4.3 mg (0.0065 mmol) catalyst, 0.052 mL of 1M (0.052 mmol) $H_2SO_4$, and 0.479 g (5.2 mmol) glycerol in 1.4 mL of aqueous dioxane solvent (1:6 V/V $H_2O$:dioxane). The catalyst used had the following formula:

The autoclave is pressurized under 80 bar of $H_2$ and heated to 200° C. After 20 hours, the autoclave is cooled to room temperature and vented. $^{13}$C-NMR spectroscopy of reaction mixtures indicates 43% conversion of glycerol with the converted fraction forming 38% 1,3-propanediol and 62% 1-propanol. When 40 bar of $H_2$ pressure was used in place of 80 bar pressure, similar results were obtained.

Example 5

The Example 4 procedure is repeated, except HCl was used in place of $H_2SO_4$. The resulting reaction mixture showed 5% conversion of glycerol to 58% 1,3-propanediol and 42% 1-propanol.

Example 6

The Example 4 procedure is repeated, except the autoclave is pressurized with a mixture of 40 bar CO and 40 bar $H_2$. The resulting reaction mixture showed 6% conversion of glycerol to 35% 1,3-propanediol and 65% 1-propanol.

Example 7

The Example 4 procedure is repeated, except the reaction was carried heated to 170° C. for 24 hours instead of 200° C. for 20 hours. The resulting reaction mixture showed 8% conversion of glycerol to 72% 1,3-propanediol and 28% 1-propanol.

Example 8

The Example 4 procedure is repeated, except with 0.0074 mmol of catalyst, 0.38 mL of 1M (0.38 mmol) $H_2SO_4$, 1.0 g (10.9 mmol) of glycerol in 3 mL of aqueous sulfolane solvent (1:1 V/V $H_2O$:sulfolane), and the reaction is heated for 24 hours. The resulting reaction mixture showed 56% conversion of glycerol to 62% 1,3-propanediol and 38% 1-propanol.

Example 9

The Example 8 procedure is repeated, except with 1.0 g of glycerol in 3 mL of aqueous dioxane (2:1 V/V $H_2O$:dioxane) and 0.0074 mmol of catalyst having the formula:

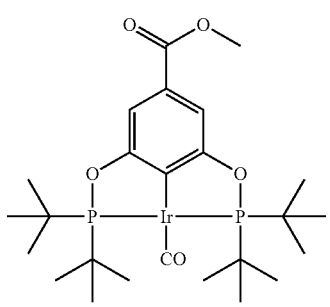

The resulting reaction mixture showed 48% conversion of glycerol to 21% 1,3-propanediol and 79% 1-propanol.

Example 10

The Example 8 procedure is repeated, except with 1.0 g of glycerol in 3 mL of $H_2O$ and 0.0074 mmol of catalyst having the formula:

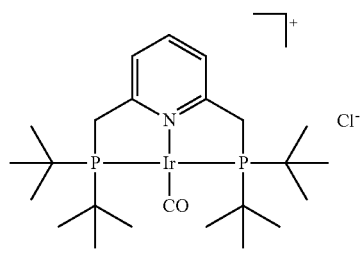

The resulting reaction mixture showed 37% conversion of glycerol to 12% 1,3-propanediol and 88% 1-propanol.

Example 11

Ir(III) pincer complexes have exhibited remarkable thermal stability and excellent catalytic efficiency in the dehydrogenation of alkane, (Gupta, M. et al., *Chem. Comm.* 1996, 2687-2688; Gupta, M. et al., *J. Am. Chem. Soc.* 1997, 119, 840-841) alcohol, diol, (Morales-Morales, D. et al., *Can. J. Chem.* 2001, 79, 823-829) and amine (Gu, X.-Q.; Chen, W.; Morales-Morales, D.; Jensen, C. M. *J. Mol. Catal. A: Chem.* 2002, 189, 119-124; Zhang, X. et al., *Chem. Comm.* 2003, 2060-2061; Bernskoetter, W. H.; Brookhart, M. *Organometallics*, 2008, 27, 2036-2045), substrates at temperatures up to 250° C. More recently, PNP- and PCP-ligated Ir(III) dihydrides were shown to rapidly hydrogenate $CO_2$ to potassium formate in aqueous KOH between 120° C. and 200° C.

In this example, the Ir pincer complex (POCOP)IrH$_2$ (1), previously reported by Brookhart and coworkers, has been utilized to catalyze the selective deoxygenation of 1,2-PD. Goettker-Schnetmann, I. et al., *J. Am. Chem. Soc.,* 2004, 126, 1804-1811; Goettker-Schnetmann, I. et al., *M. Organometallics,* 2006, 25, 3007-3011. The hydrolytic and thermal stability of the (POCOP)Ir core enabled detailed optimization studies in which key variables that controlled deoxygenation selectivity were identified. In addition, the speciation of the catalyst was investigated, which, as provided by the present invention, led to the discovery of the superior and water- and air-stable Ir(I) carbonyl precatalyst 2. The significant stability of this catalyst system combined with high selectivity points to the viability of catalytic polyol deoxygenation processes.

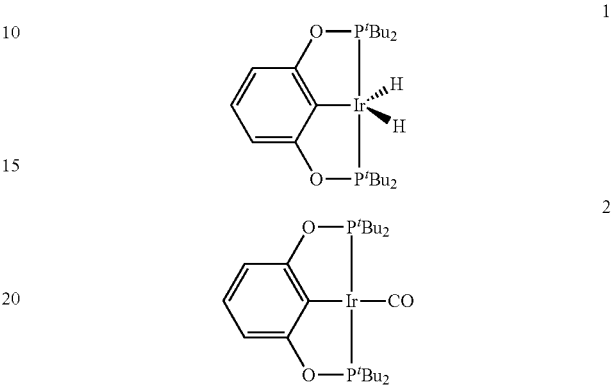

Hydrogenation of 1,2 Propanediol. Using (POCOP)IrH$_2$ and trifluoromethanesulfonic acid, 1,2-propanediol (1,2 PD) was reduced to n-propanol in up to 95% yield in aqueous dioxane at 125° C. under 100 psi H$_2$. The mild conditions of the reaction and the high selectivity observed are extraordinary. Even more remarkable is the stability of this catalyst to the aqueous environment. In fact, the presence of water is actually required to achieve high deoxygenation selectivity and hydrogenation efficiency, which also increased as the acid concentration in the reaction system was decreased.

As shown in FIG. 1, the combined yield of 1-propanol and n-propyl ether generated in the Ir-catalyzed deoxygenation of 1,2-propanediol (1,2-PD) increased from 2% to 95% as the percent of water initially present in the solution was increased (from 0-20% by volume) and as the acid concentration was reduced (from 1 to 0.05 equivalents with respect to 1,2-PD).

Reactions containing no water and/or more than 0.25 equivalents of triflic acid gave poor selectivity toward the n-alcohol and yielded up to fifteen distinct products which were identified by $^1$H NMR spectroscopy and/or GC/MS. Several of these products along with pathways that have been proposed for their generation are shown in Scheme 1. In addition to compounds shown in Scheme 1, dipropylene glycol, dipropyl ether, and isopropyl ether were also identified and reasonably result from condensation of the respective alcohols. In addition, some decomposition of the dioxane solvent was observed leading to the generation of ethanol and ethylene glycol, which were not observed in the absence of dioxane. With the exception of propane, isomers of 2,5- and 2,6-dimethyldioxane, and dipropoxypropane, which were observed by NMR spectroscopy and/or GC-MS, all major byproducts were quantified using a GC assay method developed and verified with authentic samples. The product profiles obtained under each set of reaction conditions were characterized by NMR spectroscopy, and GC-MS and/or comparison to authentic compounds prepared by independent synthesis.

Scheme 1. Conversion of propanediol to 1-propanol and the competing pathways to various byproducts observed.

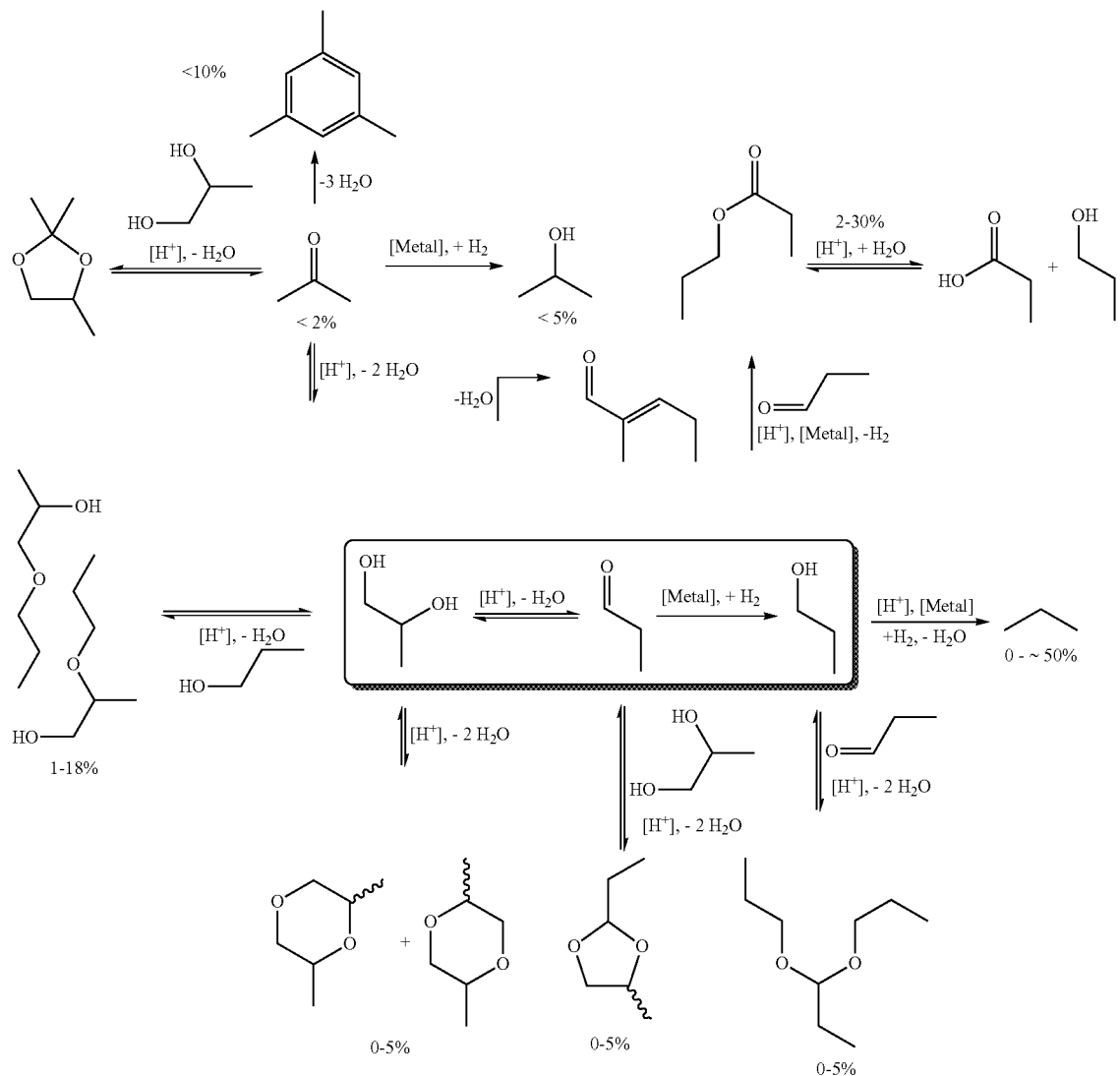

Figure 2:
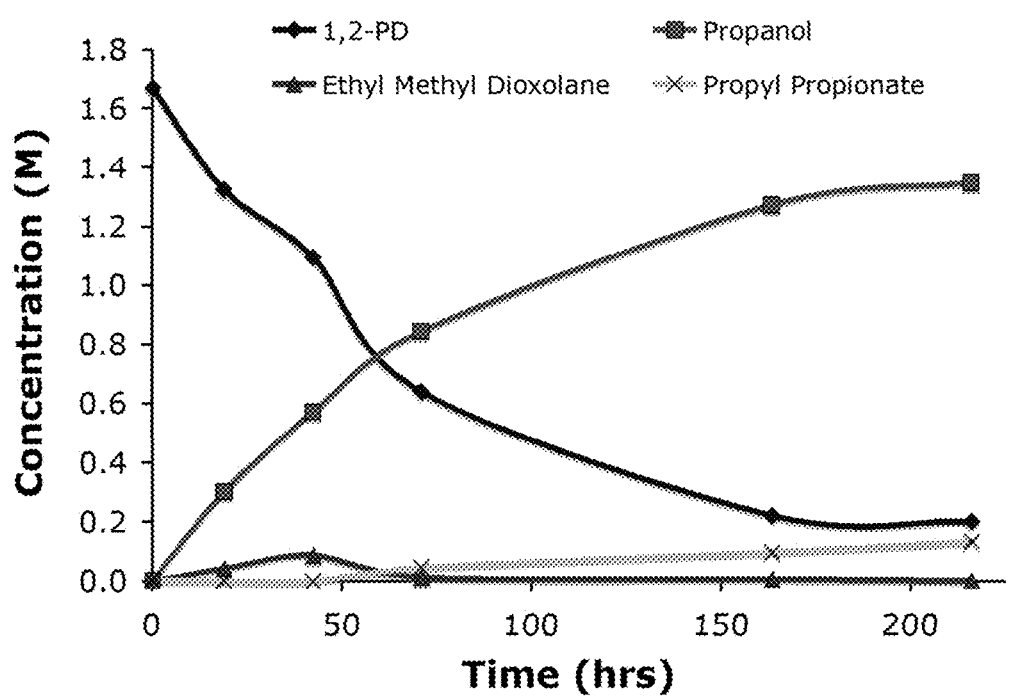
FIG. 2 shows a time course of 1,2-propanediol deoxygenation showing reversible formation of ethyl methyl dioxolane.

The selectivity trend shown in FIG. 1 may be attributed to both thermodynamic and kinetic factors. Higher water concentration will give lower steady state concentrations of dehydrated species and thus limit formation of byproducts arising from condensation reactions (see Scheme 1). The reversible formation of condensation byproducts, such as ethyl methyl dioxolane, in aqueous solution (>10% water) is apparent in the kinetic trace of the reaction mixture (FIG. 2). It is reasonable to suggest that the relative rate of hydrogenation of propionaldehyde to that of dehydration is much higher at the optimal reaction conditions, leading to lower steady-state concentrations of aldehyde intermediate and minimal competition from subsequent acid-catalyzed conversions. In fact, no propionaldehyde intermediate is observed by NMR spectroscopy in reaction mixtures containing more than 20% water (by volume) and 0.10 equivalents of acid or less. In these cases, the propionaldehyde intermediate is rapidly hydrogenated to n-propanol by the Ir catalyst with excellent overall selectivity. As the acid concentration increases, the acid-catalyzed pathways can become competitive with hydrogenation resulting in significant formation of ether, ester, carboxylic acid, and aromatic byproducts. In the latter case, mesitylene is formed via acid-catalyzed trimerization of the ketone intermediate at high acid concentration. This mechanism was confirmed by an experiment using 1,2-pentanediol, which leads to formation of 1,3,5-tripropylbenzene.

Carboxylate containing byproducts were significant, formed in up to 30% yield in reactions containing more than 0.5 equivalents of triflic acid. Carboxylic acid could result from dehydrogenation of 1,1-geminal diols produced in the reaction (Scheme 2a). However, dehydrogenative coupling of the aldehyde intermediate with the 1-alcohol product, followed by acid-catalyzed hydrolysis (Scheme 2b) would also be consistent with experimental findings.

We have examined the iridium catalyzed hydrogenation of propionaldehyde in dioxane solvent. In addition to 1-propanol, we find that propyl propionate is formed, with the amount of ester formed increasing with the yield of 1-propanol. No ester is observed in a control experiment starting from propionaldehyde in the absence of dihydrogen, which rules out a Tischenko-type aldehyde coupling. However, addition of water to a solution of propionaldehyde and (POCOP)IrH$_2$ under Ar, leads to formation of equimolar amounts of propionic acid and propanol, indicating that under aqueous conditions propioaldehyde can act as a hydrogen acceptor in the dehydrogenation of its 1,1-propanediol hydration product (Scheme 2b).

Scheme 2. Proposed pathways to propionic acid:
(a) dehydrogenation of 1,1-propanediol.
(b) dehydrogenative coupling of propionaldehyde and 1-propanol.

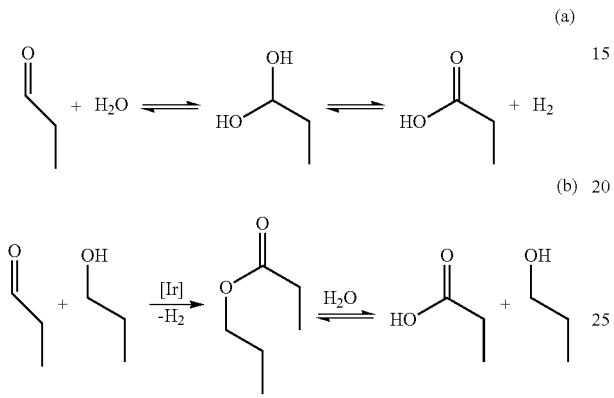

Figure 3:
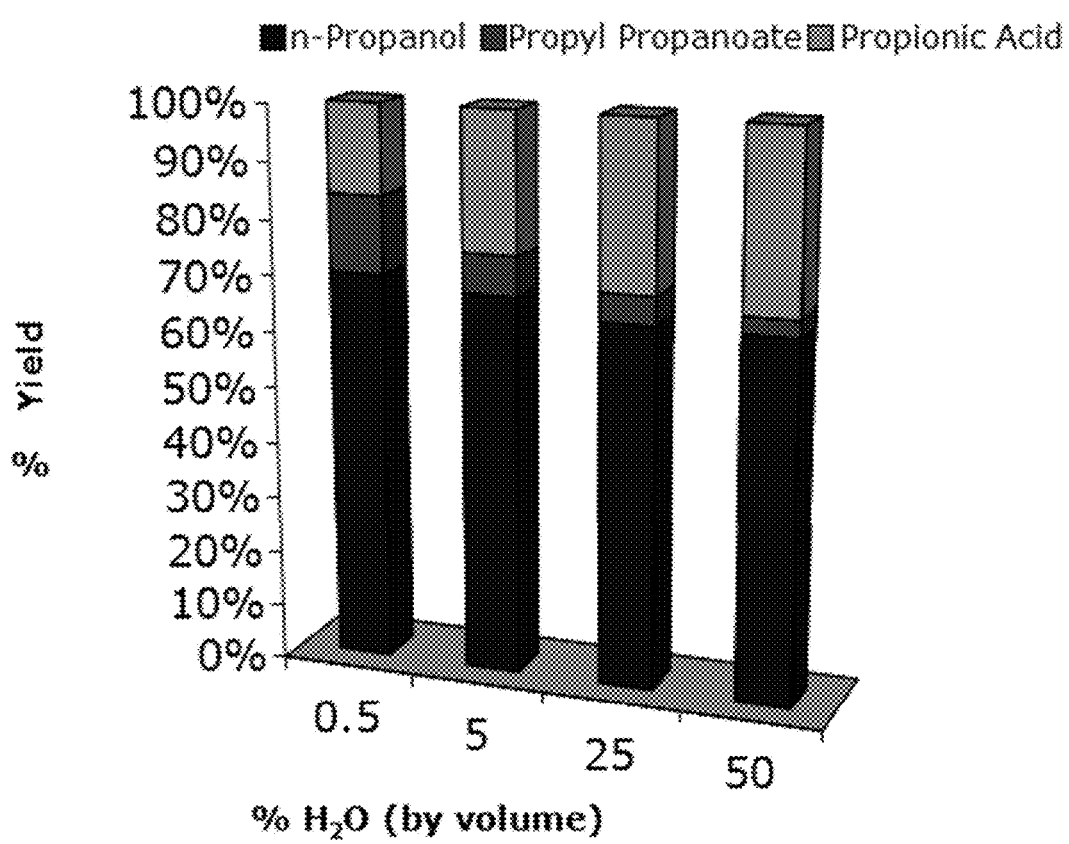
FIG. 3 shows percent yield of n-propanol, propyl propionate, and propionic acid in the (POCOP)IrH$_2$-catalyzed hydrogenation of propionaldehyde as a function of % water by volume (1.5 mol % (POCOP)IrH$_2$, 100 psi H$_2$, 50° C., aqueous dioxane).

The yield of carboxylate products decreases with increasing hydrogen pressure, but trace amounts of propionic acid (<1.5%) are observed at pressures as high as 40 bar in the aqueous-phase diol deoxygenations. Examination of the hydrogenation of propionaldehyde to 1-propanol shows that the selectivity decreases with increasing water content (FIG. 3), due to the competing dehydrogenation pathways to propionic acid (Scheme 2). This effect of increased water is opposite of that previously noted for the diol substrate, where deoxygenation selectivity improves with a concomitant decrease in carboxylic acid yield with more water. These opposing trends observed for the overall deoxygenation reaction and the hydrogenation step can be attributed to the low steady state concentrations of aldehyde intermediate generated in the course of the reaction.

Effect of Temperature and Pressure. Increasing the reaction temperature from 125° C. to 200° C. at 100 psi H$_2$ led to a significant decrease in 1,2-propanediol deoxygenation selectivity from 95% to 12% 1-propanol, even in 20% aqueous dioxane. At this higher temperature, the product mixture also contained propionaldehyde (17%), 2-methyl 2-pentenal (8%), ethyl methyl dioxolane (6%), propylene glycol propyl ether (2%), dipropylene glycol (6%), propionic acid (3%) and acetone (2%) upon complete consumption of the diol. The high concentration of propionaldehyde suggests that the rate of the aldehyde hydrogenation step is not competitive with alternative reversible reactions of the aldehyde at this temperature. Notably, at 185° C., increasing the hydrogen pressure to 600 psi restored the deoxygenation selectivity to 90% 1-propanol. The only byproducts observed were propionaldehyde (0.5%), propylene glycol propyl ether (PGPE, 1%), dipropylene glycol (3%) and a trace amount of ethanol from dioxane decomposition.

The use of only water (30%) as solvent was explored. Limited screening showed that yields of PGPE (7%) and dipropylene glycol (5%) were significantly higher (results from 66% conversion using 30% water, 0.5 mol % Ir, and 0.6% triflic acid at 185° C. for 6 hours with 100 psi H$_2$). The selectivity for 1-propanol remained relatively high (43% yield), and only minor amounts of dipropyl ether (1.6%), isopropanol (0.4%), propionaldehyde (0.1%), propionic acid (0.2%) and ethyl methyl dioxolane (0.4%) were observed. Further optimization to improve selectivity and efficiency with variation of acid concentration, hydrogen pressure and temperature of the reactions is in progress.

Catalyst Speciation. Monitoring catalyst speciation reveals that the (POCOP)IrH$_2$ precatalyst is not observed during the course of the deoxygenation reaction. Upon completion of the reaction, two species were identified by $^{31}$P-NMR spectroscopy, with a resonance at δ=199 assigned to the previously reported carbonyl complex (POCOP)Ir(CO), (2). Zhang, X.; Fried, A.; Knapp, S.; Goldman, A. S. *Chem. Comm.* 2003, 2060-2061. A resonance at δ=183 is attributed to trans-(POCOP)—Ir(CO)(H)$_2$, (3), which also exhibits a triplet hydride resonance in the $^1$H-NMR spectrum at −9.53 ppm ($^2J_{P-H}$=15 Hz).

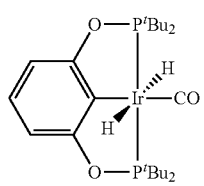

3

Figure 4:
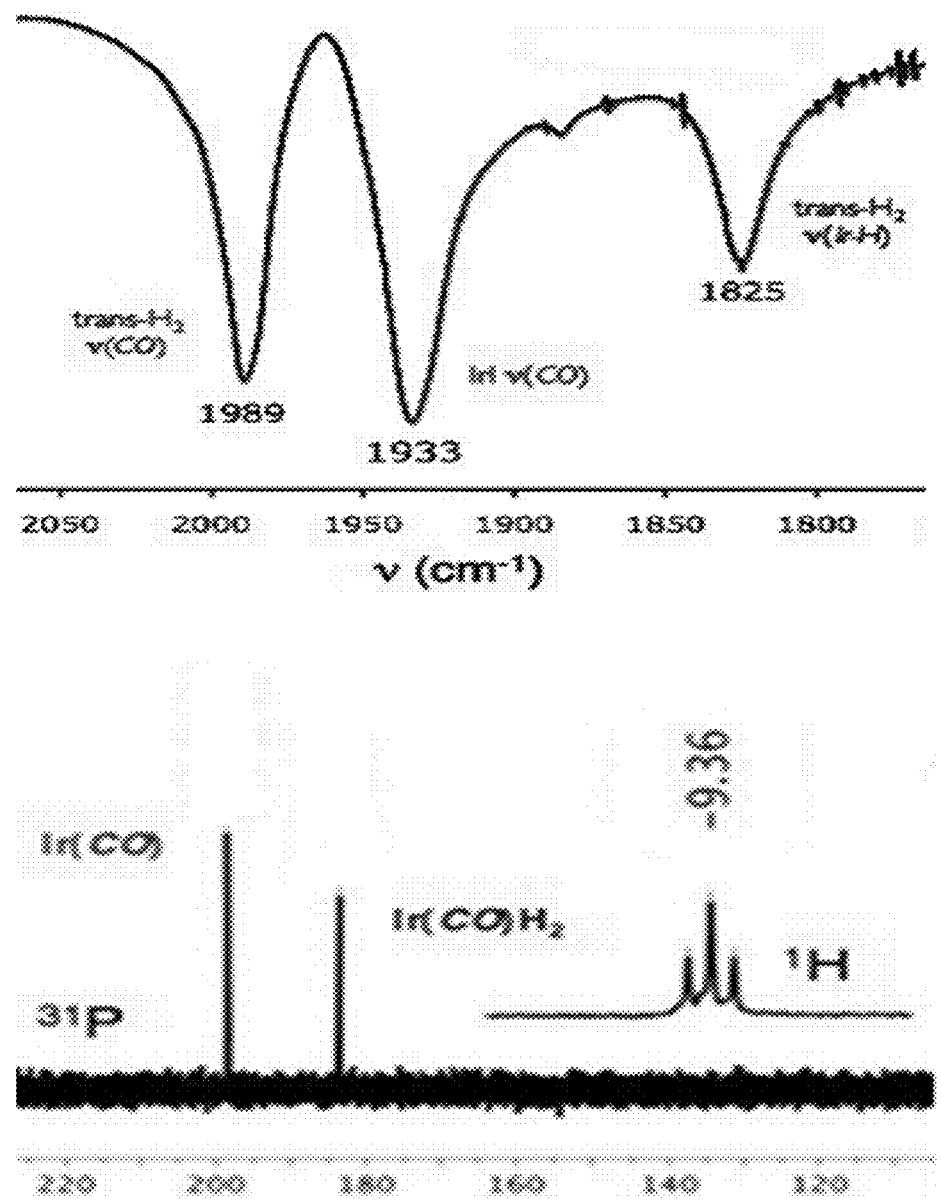
FIG. 4 shows data for a catalyst sample isolated from a deoxygenation reaction. Bottom: $^1$H and $^{31}$P{$^1$H} NMR spectra. Top: IR spectrum (carbonyl region, KBr disc).

Upon completion of the deoxygenation reactions, an orange crystalline solid was isolated from the reactor. Dissolution of this solid gave the $^{31}$P- and $^1$H-NMR spectra shown in FIG. 4. IR spectra of these crystals show CO bands at 1933 cm$^{-1}$ and 1988 cm$^{-1}$, attributed to the Ir(I) and Ir(III) carbonyls, respectively. The Ir—H stretching frequency was observed at 1825 cm$^{-1}$. These observations suggest that a mixture of complexes 2 and 3 crystallized from the reaction.

Consistent with previous reports, we find that (POCOP)IrH$_2$ is rapidly converted to (POCOP)Ir(CO) upon exposure to CO at room temperature. Zhang, X.; Fried, A.; Knapp, S.; Goldman, A. S. *Chem. Comm.* 2003, 2060-2061. In contrast, addition of CO to (POCOP)IrH$_2$ in toluene at 0° C. resulted in a mixture of the Ir(I) and Ir(III) carbonyls, as indicated by the two $^{31}$P signals at δ 199 and δ 183 and a triplet ($^2J_{P-H}$=15 Hz) hydride resonance at −9.53 ppm ($^2J_{P-H}$=15 Hz).

In the hydrogenation reactions examined, the Ir carbonyl complexes 2 and 3 are accessed via decarbonylation of the aldehyde intermediate. The generation of 2 and 3 is even faster when starting with the aldehyde as the substrate. This reactivity is analogous to a previous report that decarbonylation of methanol led to cationic trans-[(PNP)Ir(H)$_2$CO]$^+$ presumably through a formaldehyde intermediate. Kloek, S. M.; Heinekey, D. M.; Goldberg, K. I. *Organometallics,* 2006, 25, 3007-3011. Similar decarbonylation reactions leading to ruthenium carbonyl complexes were reported by Schlaf and coworkers in the course of hydrogenation of 1,2 hexanediol. Taher et al., *Chem. Eur. J.,* 2010 15, 10132-10143.

Noting that (POCOP)Ir(CO) was observed in the catalytic deoxygenation reactions, we tested this species as a precatalyst. (POCOP)Ir(CO) has a significant advantage over (POCOP)IrH$_2$ in that it is air-stable. The presence of water was found to accelerate the rate of hydrogenation. Water likely aids in the formation of the active catalyst from (POCOP)Ir(CO) via a proton-assisted oxidative addition of hydrogen affording trans-(POCOP)Ir(CO)(H)$_2$. Initial protonation of the basic (POCOP)Ir(CO) complex leads to formation of a cationic Ir(III) monohydride. Subsequent association of dihydrogen, followed by deprotonation of the cationic species results in formation of the trans-dihydride (Scheme 3). Proton-assisted hydrogen addition to the analogous (PONOP)Ir(CH$_3$) complex affording a trans-dihydride complex was recently demonstrated. Findlater, M. et al., *J. Am. Chem. Soc.* 2010 132, 4534-4535.

Scheme 3. Proposed mechanism for water assisted hydrogen addition to (POCOP)Ir(CO).

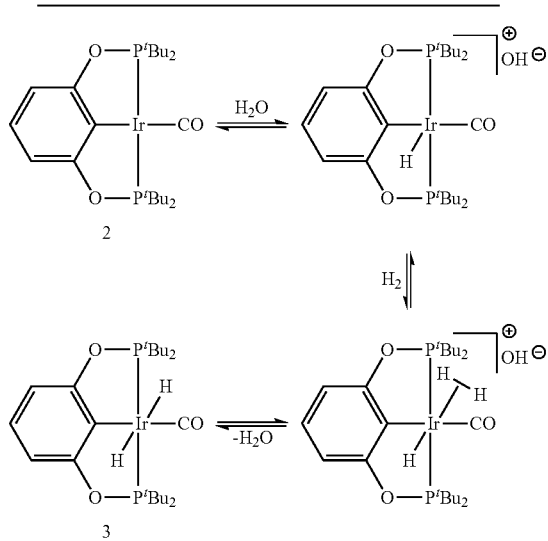

Efficient hydrogenolysis of 1,2 propanediol to 1-propanol is catalyzed by acid in tandem with a pincer iridium complex. The catalyst reservoir species is an Ir(I) carbonyl complex. The presence of water in the reaction mixture gives improved selectivity for 1-propanol.

General Procedures. All experiments were performed under an Argon atmosphere using standard glovebox or Schlenk techniques. All solvents were dried using appropriate drying agents. Alcohol and aldehyde substrates were purchased from Aldrich and used as received. The compounds (POCOP)IrH$_2$, (POCOP)Ir(H)(Cl), and (POCOP)Ir(CO) were prepared as described in the literature. Goettker-Schnetmann, I. et al., *J. Am. Chem. Soc.*, 2004, 126, 1804-1811; Goettker-Schnetmann, I. et al., *M. Organometallics*, 2006, 25, 3007-3011.

All deoxygenation reactions were prepared in a glovebox under an atmosphere of argon in J-Young screw cap NMR tubes or Parr reactors. $^1$H-NMR spectra were obtained using a Bruker 500 MHz or 300 MHz spectrometer, and were integrated relative to the toluene internal standard resonances. Quantitative GC analyses were performed using a Hewlett Packard 4890 Gas Chromatograph using a DB wax column, and GC-MS data were obtained using a Hewlett Packard 5971A spectrometer. IR spectra were obtained using a Bruker Vector 33 FT-IR spectrometer.

Deoxygenation of 1,2 PD. Experiments conducted to investigate the effect of acid and water were performed in J-Young tubes as follows: (POCOP)IrH$_2$ (0.005 g, 0.009 mmol) was added to an NMR tube. The remaining reagents were added in appropriate volume in order to achieve a total volume of 0.50 mL with a 1,2-propanediol concentration of 1.36M while varying the acid (0.050-1.00 equivalents relative to 1,2-PD) and water (0-20% by volume) content. Dioxane (0.280-0.437 mL) was added to give a dark red-brown homogeneous solution, which lightened upon addition of 1,2-propanediol (0.050 mL, 0.681 mmol) and water (0-0.100 mL). Toluene was added as an internal standard. (0.010 mL, 0.096 mmol) Finally, trifluoromethanesulfonic acid (0.003-0.060 mL, 0.034-0.678 mmol) was added to the reaction mixture using a micropipet to give a light orange solution, and the tubes were sealed. The J-Young tubes were freeze-pump-thawed three times prior to addition of 100 psi of H$_2$. Pressurized tubes were then heated to 125° C. At the end of the reaction, the tubes were cooled to room temperature. The mixture was analyzed by gas chromatography.

Reactions conducted at pressures higher than 100 psi H$_2$ were carried out in Parr reactors. Water, acid, catalyst, and diol concentrations were varied. The order of additions was unchanged. In these cases, the reactor was purged with hydrogen gas for one minute prior to charging with 40 bar H$_2$. At the end of the reaction, the Parr reactor was allowed to cool to room temperature and then cooled in a dry ice acetone prior to slow venting of the hydrogen atmosphere to minimize the mass loss. The average mass lost was 10%.

Propionaldehyde Hydrogenation. (POCOP)IrH$_2$ (0.0017 g, 0.0029 mmol) was added to a J-Young tube followed by dioxane (0.198-0.448 mL). Propionaldehyde (0.0500 mL, 0.687 mmol) was added and the red-brown solution turned orange. Toluene (2.00 μL, 0.0187 mmol) was added as an internal standard, and varying amounts of water were added (2.50 μL-250 μL). The J-Young tube was sealed under an Ar atmosphere and freeze-pump-thawed on a vacuum line. The tube was pressurized with 100 psi H$_2$ and heated to 125° C. The reaction was monitored by NMR spectroscopy and the yields were determined by integration relative to toluene.

Example 12

This example describes one example of a waste glycerol purification procedure. To a 5 mL stirring solution of glycerol from biodiesel production is added 3 mL of 1 M sulfuric acid dropwise until the solution turns into a milky white suspension. The solution is stirred for an additional 5 minutes before allowing layers to separate overnight. Upon separation, the solution affords a clear, colorless bottom layer and a tan cloudy top layer. The clear, colorless bottom layer is collected and filtered to remove any solids. Analyzing a neat solution by $^{13}$C-NMR spectroscopy shows only signals for glycerol and methanol.

The example further includes an example deoxygenation of purified waste glycerol. A 30 CC Hastelloy autoclave with magnetic stirring is charged with 0.3 g of the purified glycerol solution in 1.7 g of dioxane solvent and 6.8 mg (0.010 mmol) catalyst of formula:

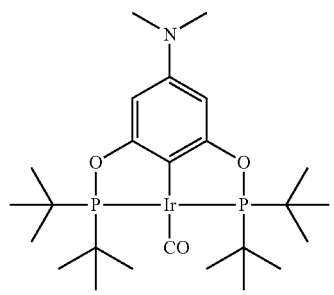

The autoclave is pressurized under 80 bar of H$_2$ and heated to 200° C. After 20 hours, the autoclave is cooled to room temperature and vented. $^{13}$C-NMR spectroscopy of reaction mixtures indicates 35% conversion of glycerol with the converted fraction forming 12% 1,3-propanediol and 88% 1-propanol.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for removing at least one alcohol group from a polyol, the method comprising:

reacting the polyol, hydrogen ($H_2$) gas, an acid, an organic solvent, and a metal pincer catalyst to form a reaction product, the polyol having at least two alcohol groups before the reacting, and the reaction product including the polyol having at least one fewer alcohol groups after the reacting, wherein the metal pincer catalyst has the general formula (I):

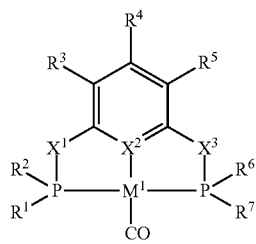

wherein $M^1$ is iridium or rhodium, wherein each of $X^1$ and $X^3$ are independently selected from —$CH_2$— or —O—, wherein $X^2$ is C or N, and wherein each of $R^1$, $R^2$, $R^3$, $R^4$, $R^5$, $R^6$, and $R^7$ are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, or general formula (II):

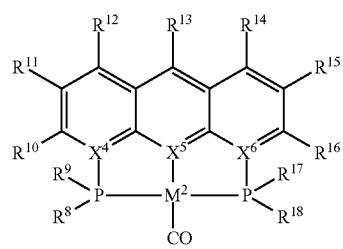

wherein $M^2$ is iridium or rhodium, wherein each of $X^4$, $X^5$ and $X^6$ are independently selected from C or N, and wherein each of $R^8$, $R^9$, $R_{10}$, $R^{11}$, $R^{12}$, $R^{13}$, $R^{14}$, $R^{15}$, $R^{16}$, $R^{17}$ and $R^{18}$ are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

or general formula (III):

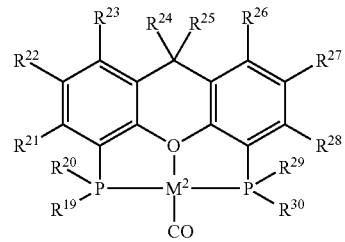

wherein $M^3$ is iridium or rhodium, and wherein each of $R^{19}$, $R^{20}$, $R^{21}$, $R^{22}$, $R^{23}$, $R^{24}$, $R^{25}$, $R^{26}$, $R^{27}$, $R^{28}$, $R^{29}$ and $R^{30}$ are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

or general formula (IV):

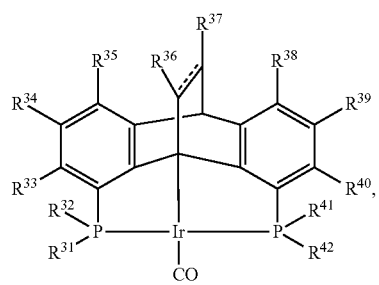

wherein each of $R^{31}$, $R^{32}$, $R^{33}$, $R^{34}$, $R^{35}$, $R^{38}$, $R^{39}$, $R^{40}$, $R^{41}$, and $R^{42}$ are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

wherein ====== is a single or double bond; and wherein each of $R^{36}$ and $R^{37}$ are independently selected from the group consisting of hydrogen, a halide, —OH, —$NH_2$, —CN, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, or wherein $R^{36}$ and $R^{37}$ are joined together to form a substituted or unsubstituted cycloalkyl, substituted or unsubstituted heterocycloalkyl, substituted or unsubstituted aryl, or substituted or unsubstituted heteroaryl.

2. The method of claim 1, wherein the polyol comprises a linear or cyclic $C_1$-$C_6$ alkane molecule substituted with the at least two alcohol groups before the reacting.

3. The method of claim 1, wherein the acid comprises a homogeneous or heterogeneous proton donor.

4. The method of claim 1, wherein the acid is selected from the group consisting of sulfuric acid, tungstic acid, phosphoric acid, hydrochloric acid and trifluoromethanesulfonic acid.

5. The method of claim 3, wherein the homogeneous acid is used at a concentration range of about 0.03M to about 0.1M.

6. The method of claim 1, wherein the organic solvent includes dioxane, sulfolane, 1,3-dimethyl-2-imidazolidinone, 1-methyl-2-pyrrolidone, 1-methyl-2-piperidone, bis(2-methoxyethyl)ether, or a combination thereof.

7. The method of claim 1, wherein $X^1$ and $X^3$ are —O—.

8. The method of claim 1, wherein $X^2$ is C.

9. The method of claim 1, wherein $R^1$, $R^2$, $R^6$, and $R^7$ are the same.

10. The method of claim 1, wherein $R^8$, $R^9$, $R^{17}$, and $R^{18}$ are the same.

11. The method of claim 1, wherein $R^{19}$, $R^{20}$, $R^{29}$, and $R^{30}$ are the same.

12. The method of claim 1, wherein $R^{31}$, $R^{32}$, $R^{41}$ and $R^{42}$ are the same.

13. The method of claim 1, wherein the metal pincer catalyst is coupled to a solid support.

14. The method of claim 1, wherein the reacting is carried out at a temperature selected from:

a temperature greater than about 160° C.;
a temperature between about 160° C. to about 220° C.; or
a temperature between about 170° C. to about 200° C.

15. The method of claim 1, wherein the polyol comprises glycerol, erythritol, xylitol, sorbitol, mannitol, glucose, fructose, or sucrose before the reacting.

16. The method of claim 1, wherein the polyol is glycerol before the reacting and the reaction product comprises 1,3-propanediol.

17. The method of claim 1, wherein the polyol is glycerol before the reacting and greater than about 60% of the glycerol is converted to 1,3-propanediol.

18. The method of claim 1, wherein the reaction product further comprises 1-propanol.

19. The method of claim 1, wherein the polyol is 1,2-propanediol before the reacting and the reaction product comprises 1-propanol.

20. The method of claim 1, wherein the metal pincer catalyst is present at about 0.05 to about 1 mole % with respect to the polyol.

21. The method of claim 1, wherein the polyol is glycerol before the reacting and, before the reacting, the method further includes combining a crude glycerol byproduct from transesterification of triglycerides with an acid to form a separated mixture comprising a crude product separated from a solution including glycerol, methanol, and methyl ester.

* * * * *